(12) United States Patent
Kim et al.

(10) Patent No.: US 11,992,492 B2
(45) Date of Patent: May 28, 2024

(54) COMPOSITION FOR PREVENTING OR TREATING CELLULAR SENESCENCE-ASSOCIATED DISEASES, CONTAINING HOMOHARRINGTONINE AS ACTIVE INGREDIENT

(71) Applicant: RESEARCH COOPERATION FOUNDATION OF YEUNGNAM UNIVERSITY, Gyeongsan-si (KR)

(72) Inventors: Jae-Ryong Kim, Daegu (KR); Eok-Cheon Kim, Wonju-si (KR); Kyong-Jin Jung, Daegu (KR); Bum-Ho Bin, Hwaseong-si (KR); You Lim Son, Daegu (KR)

(73) Assignee: RESEARCH COOPERATION FOUNDATION OF YEUNGNAM UNIVERSITY, Gyeongsan-si (KR)

( * ) Notice: Subject to any disclaimer, the term of this patent is extended or adjusted under 35 U.S.C. 154(b) by 274 days.

(21) Appl. No.: 17/413,101

(22) PCT Filed: Oct. 11, 2019

(86) PCT No.: PCT/KR2019/013371
§ 371 (c)(1),
(2) Date: Jun. 11, 2021

(87) PCT Pub. No.: WO2020/122391
PCT Pub. Date: Jun. 18, 2020

(65) Prior Publication Data
US 2022/0023309 A1 Jan. 27, 2022

(30) Foreign Application Priority Data
Dec. 13, 2018 (KR) .................. 10-2018-0161042

(51) Int. Cl.
A61K 31/55 (2006.01)
A61P 13/12 (2006.01)
A61P 29/00 (2006.01)

(52) U.S. Cl.
CPC .............. *A61K 31/55* (2013.01); *A61P 13/12* (2018.01); *A61P 29/00* (2018.01)

(58) Field of Classification Search
CPC .................. A61K 31/55; A61P 13/12
See application file for complete search history.

(56) References Cited

U.S. PATENT DOCUMENTS
2010/0278784 A1  11/2010  Pojasek et al.

FOREIGN PATENT DOCUMENTS

| CN | 1511531 A | 7/2004 | |
|---|---|---|---|
| KR | 10-2009-0130129 A | 12/2009 | |
| KR | 10-2014-0092544 A | 7/2014 | |
| KR | 10-2016-0017603 A | 2/2016 | |
| WO | WO-2004009030 A2 * | 1/2004 | ............. A61K 31/55 |
| WO | WO-2014159500 A1 * | 10/2014 | ........... A23L 29/035 |
| WO | WO-2018141678 A1 * | 8/2018 | ........... A61K 31/395 |

OTHER PUBLICATIONS

Segura et al (Trends in cell Biology, 2018; 28(6):436-453, published Jun. 2018) (Year: 2018).*
Ovadya et al (J Clin Invest. 2018;128(4):1247-1254, published Apr. 2018). (Year: 2018).*
Joung et al (Journal of Pathology and Translational Medicine 2018; 52: 323-330, published online Aug. 19, 2018) (Year: 2018).*
STNext (CAS Registry No. 26833-87-4, STN date: Nov. 16, 1984) (Year: 1984).*
Li, Xiaolei, et al. "Homoharringtonine prevents surgery-induced epidural fibrosis through endoplasmic reticulum stress signaling pathway." European journal of pharmacology, 815, 2017 (pp. 437-445).
International Search Report issued on Feb. 7, 2020 in counterpart International Patent Application No. PCT/KR2019/013371 (2 pages in English and 2 pages in Korean).

\* cited by examiner

*Primary Examiner* — Rayna Rodriguez
(74) *Attorney, Agent, or Firm* — NSIP Law

(57) ABSTRACT

The present invention relates to a composition for preventing or treating cellular senescence-associated diseases comprising homoharringtonine as an active ingredient, and it was confirmed that the composition comprising homoharringtonine as an active ingredient exhibits a senolytics effect of selectively killing aging-induced fibroblasts and renal tubular cells, whereas aging-induced vascular endothelial cells and epithelial melanocytes and retinal pigmented epithelial cells, and exhibits a senomorphics effect of restoring the function and morphology of cells, and thus the homoharringtonine acts differently depending on the type of cells to effectively prevent or treat senile eye disease, tissue fibrosis disease, atherosclerosis, osteoarthritis, degenerative brain disease, chronic skin damage, obesity and diabetes caused by cellular aging and can be provided as a composition for whitening skin and life extension.

4 Claims, 22 Drawing Sheets

HK2

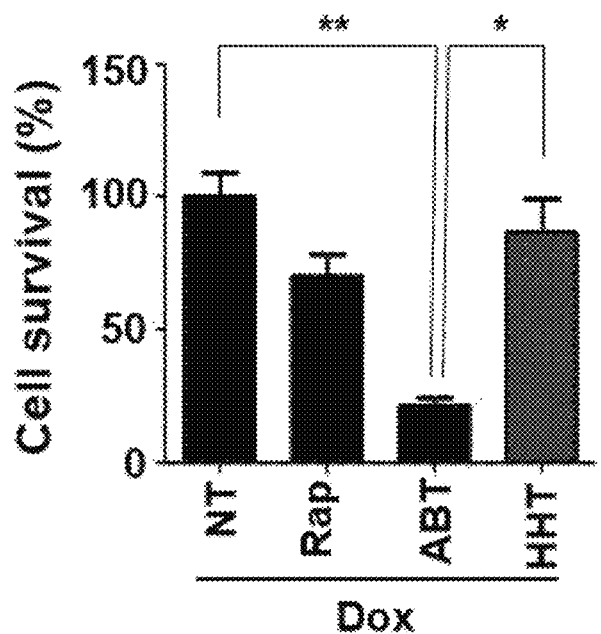

COMPOSITION FOR PREVENTING OR TREATING CELLULAR SENESCENCE-ASSOCIATED DISEASES, CONTAINING HOMOHARRINGTONINE AS ACTIVE INGREDIENT

CROSS REFERENCE TO RELATED APPLICATIONS

This application is a U.S. National Stage Application of International Application No. PCT/KR2019/013371, filed on Oct. 11, 2019, which claims the benefit under 35 USC 119(a) and 365(b) of Korean Patent Application No. 10-2018-0161042, filed on Dec. 13, 2018, in the Korean Intellectual Property Office, the entire disclosure of which is incorporated herein by reference for all purposes.

TECHNICAL FIELD

The present invention relates to a composition for preventing or treating cellular senescence-associated diseases comprising as an active ingredient homoharringtonine, which acts differently depending on the type of senescent cells.

BACKGROUND ART

Senescent cells accumulate in individual tissues and organs with aging, and accumulation of senescent cells not only induces changes in the function and structure of tissues and organs due to aging, but also plays an important role in the etiology of various senescence-associated diseases such cancer, diabetes, obesity, tissue fibrosis, senile eye diseases, cardio-cerebrovascular disease, degenerative brain disease, osteoarthritis, skin aging and chronic skin wounds, etc. Therefore, it has been suggested that delaying or overcoming aging is the most effective method for the prevention and treatment of senescence-associated diseases such as cancer, diabetes, and cardiovascular disease.

Rapamycin, SIRT1 activator, calorie-limiting mimetic, AMPK activator, and telomerase activator are promising as aging control drugs. In addition, recently, senotherapeutics, which target senescent cells, have been developed and their efficacy has been reported at the cellular level and in animal models. Senotherapeutics are divided into senolytics, which selectively kill only senescent cells, and senomorphics, which restore the function or morphology of senescent cells like young cells.

Quercetin and dasatinib, which are Bcr-Abl protein kinase inhibitors, ABT263 and ABT737, which are Bcl-2 kinase inhibitors, and A1331852 and A1155463, which are BCL-XL inhibitors, and UBX0101, which is an MDM2/p53 inhibitor, FOXO4-DRI, which is p53 inhibitor, and 17-DMAG, which is HSP90 inhibitor, have been recently reported as senolytics. As senomorphics, mTOR inhibitors such as rapamycin, IKK/NFkB inhibitors, free radical scavengers and JAK inhibitors have been reported.

Accordingly, research and development for preventing or treating senescence-associated diseases are actively progressing through the development of senotherapeutics that target senescence and senescent cells.

Homoharringtonine (omacetaxine mepesuccinate) is a single component of a natural product extracted from *Cephalotaxus harringtonii*, and is commercially available as a treatment for chronic myeloid leukemia. Its mechanism of action is known to act to inhibit protein translation by binding to ribosomes, but the action of senotherapeutics has not yet been reported.

DISCLOSURE

Technical Problem

The present invention provides a composition comprising homoharringtonine as an active ingredient to selectively kill senescent cells or restore the function and morphology of senescent cells to provide a composition for improving or treating diseases caused by cellular aging.

Technical Solution

The present invention provides a senolytics composition comprising homoharringtonine as an active ingredient.

The present invention provides a senomorphics composition comprising homoharringtonine as an active ingredient.

The present invention provides a pharmaceutical composition for preventing or treating cellular senescence-associated diseases comprising homoharringtonine as an active ingredient.

The present invention provides a composition for whitening skin comprising homoharringtonine as an active ingredient.

In addition, the present invention provides a composition for improving aging or extending life comprising homoharringtonine as an active ingredient.

Advantageous Effects

According to the present invention, it was confirmed that a composition comprising homoharringtonine as an active ingredient exhibits a senolytics effect of selectively killing aging-induced fibroblasts and renal tubular cells, whereas aging-induced vascular endothelial cells and epithelial melanocytes and retinal pigmented epithelial cells, and exhibits a senomorphics effect of restoring the function and morphology of cells, and thus the homoharringtonine acts differently depending on the type of cells to effectively prevent or treat obesity, diabetes, degenerative neurological disease, osteoarthritis, atherosclerosis, chronic skin damage, senile eye disease and tissue fibrosis disease caused by cellular aging and can be provided as a composition for whitening skin and life extension.

DESCRIPTION OF DRAWINGS

FIG. 1A shows a result of treatment with 100 nM rapamycin, 100 nM ABT263 and 100 nM homoharringtonine on young fibroblasts (HDF) and premature senescent fibroblasts by doxorubicin, and SAβG activity staining after 4 days; FIG. 1B shows a result of the SAβG activity level; and FIG. 10 shows a result of confirming cell survival. HDF=human dermal fibroblasts, Young=young cells, Dox=doxorubicin, NT=0.01% DMSO, Rap=100 nM rapamycin, ABT=100 nM ABT263, HHT=100 nM homoharringtonine. (** $p<0.01$, * $p<0.05$).

FIG. 2A shows a result of treatment with 100 nM ABT263 and 100 nM homoharringtonine on young fibroblast (HDF) and replicative senescent fibroblasts, and SAβG activity staining after 4 days; FIG. 2B shows a result of the cell survival according to the concentration of homoharringtonine; FIG. 2C shows a result of confirming the cytotoxic effect through LDH activity analysis; and FIG. 2D shows a result of the expression levels of PARP and caspase-3, which are apoptosis-related proteins by Western blot analysis. HDF=human dermal fibroblasts, Young=young cells, Senescent=replicative senescent cells, NT=0.01% DMSO, ABT=100 nM ABT263, HHT=100 nM homoharringtonine. (*, p<0.05; , p<0.01 vs NT; , p<0.01 vs Young).

FIG. 3A shows a cell photograph of treatment with 100 nM ABT263, 100 nM rapamycin, 100 nM homoharringtonine on premature senescent human renal tubular cells (HK2) by doxorubicin, and confirming the cell survival level after 4 days; and FIG. 3B shows a result of analyzing CCK-8. HK2=human tubular epithelial cells, Dox=doxorubicin, NT=0.01% DMSO, Rap=100 nM rapamycin, ABT=100 nM ABT263, HHT=100 nM homoharringtonine. (**, p<0.01).

FIGS. 4A-4C show results of confirming the senomorphics action of homoharringtonine in premature senescent vascular endothelial cells by doxorubicin; FIG. 4A shows a staining picture of treatment with a 100 nM rapamycin, 100 nM ABT263 and 100 nM homoharringtonine on young vascular endothelial cells (HUVEC) and premature senescent vascular endothelial cells by doxorubicin, and confirming SAβG activity after 4 days; FIG. 4B shows a result of the level of SAβG activity staining; and FIG. 4C shows a result of confirming cell survival. HUVEC=human umbilical vascular endothelial cells, Young=young cells, Dox=doxorubicin, NT=0.01% DMSO, Rap=100 nM rapamycin, ABT263=100 nM ABT263, HHT=100 nM homoharringtonine. (*, p<0.05; **, p<0.001).

FIG. 5A shows a result of staining picture of treatment with 100 nM rapamycin and 100 nM homoharringtonine on young vascular endothelial cells (HUVEC) and replicative senescent vascular endothelial cells, and confirming SAβG activity after 4 days; FIG. 5B shows a result of the SAβG activity staining level; FIG. 5C shows a result confirming the expression level of p53 and p16 protein by Western blot analysis; FIG. 5D shows a result of confirming the cell proliferation rate according to the concentration of homoharringtonine; and FIG. 5E shows a result of confirming the cytotoxic effect through LDH activity analysis. HUVEC=human umbilical vascular endothelial cells, Young=young cells, Senescent=replication senescent cells, NT=0.01% DMSO, Rap=100 nM rapamycin, ABT=100 nM ABT263, HHT=100 nM homoharringtonine. (*, p<0.05; **, p<0.01).

FIG. 6A shows a result of staining picture of treatment with 100 nM rapamycin and 100 nM homoharringtonine on young retinal pigmented epithelial cells (ARPE) and premature senescent retinal pigmented epithelial cells by doxorubicin, and confirming SAβG activity after 4 days; FIG. 6B shows a result of the level of SAβG activity; FIG. 6C shows a result of confirming p53 and p16 protein expression levels by Western blot analysis; FIG. 6D shows a result of confirming the cell proliferation level in a concentration-dependent manner of homoharringtonine; and FIG. 6E shows a result of confirming the cytotoxic effect through LDH activity analysis. ARPE=adult retinal pigmented epithelial cells, Young=young cells, Dox=doxorubicin, NT=0.01% DMSO, ABT=100 nM ABT263, HHT=100 nM homoharringtonine. (**, p<0.01).

FIG. 7A shows a result of staining picture of treatment with 100 nM rapamycin and 100 nM homoharringtonine on young melanocytes (HEM) and replicative senescent melanocytes, and confirming SAβG activity after 4 days; FIG. 7B shows a result of confirming the survival level of replicative senescent cells; FIG. 7C shows a result of the level of SAβG activity staining of replicative senescent cells; FIG. 7D shows a result of confirming the number of senescent cells according to the protrusion and cell size (>30 μm); and FIG. 7E shows a result of confirming the effect of homoharringtonine on cell proliferation of young cells. HEM=human epidermis melanocytes, Young=young cells, Senescent=replicative senescent cells, NT=0.01% DMSO, Rap=100 nM rapamycin, HHT=100 nM homoharringtonine, BT=before HHT treatment. (**, p<0.01 vs NT).

FIG. 8B shows a result of confirming the weight change before the experiment and after kidney resection, and FIG. 8C shows a result of plasma creatinine concentration and FIG. 8D shows a result of the plasma BUN concentration; FIG. 8E shows a result of hematoxylin-eosin staining, trichrome staining and PAS staining of the tissue sample, FIG. 8F shows a result of the degree of fibrosis of the tissue after trichrome staining in the sample; FIG. 8G shows a result of confirming the degree of cellular aging in the tissue by Sudan Black B staining; FIG. 8H shows a result of confirming the lipid peroxide level in the tissue, FIG. 8I shows a result of performing MDA analysis in the tissue, FIG. 8J shows a result of confirming the level of superoxides in the tissue, and FIG. 8K shows a result of confirming the expression level of 4-HNE and p16 protein in the tissue by Western blot analysis; and FIG. 8L shows a result of Western blot analysis of tissue proteins, and FIG. 8M shows a result of densitometry analysis of western blot result. Sham=no ischemia-reperfusion injury, PBS=ischemia-reperfusion injury, HHT=ischemia-reperfusion injury followed by homoharringtonine intraperitoneal injection, UIRI=left kidney ischemia-reperfusion injury, UNx=right kidney resection, PAS=periodic acid-Schiff, MDA=malondialdehyde, 4-HNE=4-hydroxynonenal, pRb=phosphorylated Rb, COL1=collagen type I, α-SMA=alpha-smooth muscle actin, SOD2=superoxide dismutase 2. (**, p<0.01, *, p<0.05).

FIG. 9A is a schematic diagram showing an experimental process; FIG. 9B shows a result of confirming a change in body weight in the experimental process; FIG. 9C shows a result of performing Hematoxylin-eosin and trichrome staining in an abdominal wall tissue sample; and FIG. 9D shows a result of confirming the thickness of peritoneal mesothelial cell layer in a tissue sample. CHG=chlorhexidine gluconate, D=homoharringtonine or DMSO intraperitoneal injection, NT=not treated, DMSO=DMSO intraperitoneal injection, HHT=homoharringtonine intraperitoneal injection (**, $p<0.01$).

BEST MODE

Figure 1A:
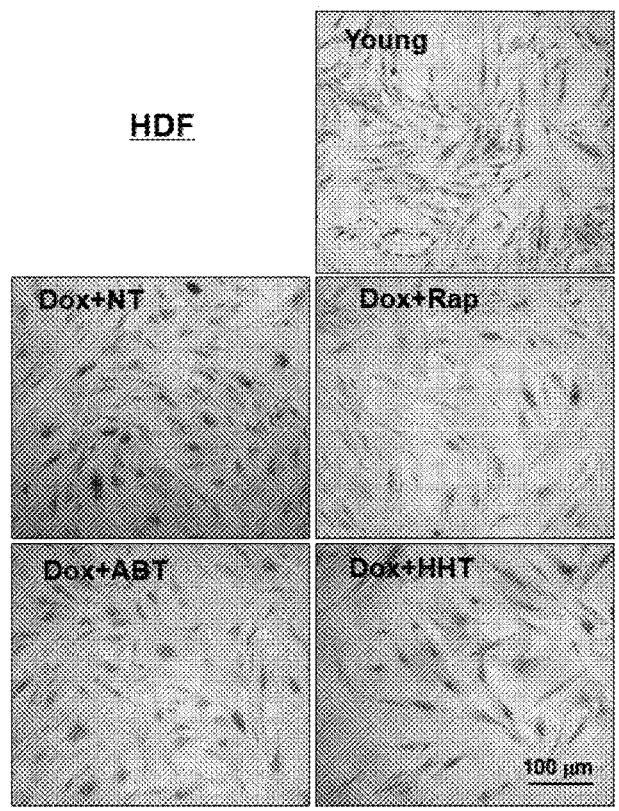
FIGS. 1A-1C show results of confirming the senolytics action of homoharringtonine in premature senescent human fibroblasts by doxorubicin.

Hereinafter, the present invention will be described in more detail.

As it is reported that when senescence cells present in tissues are removed from animal models, the structure and function of tissues and organs due to aging are improved to treat senescence-associated diseases, the health life is increased, the inventors of the present invention conducted research on senotherapeutics targeting senescent cells to confirm that homoharringtonine acts differently depending on the type of senescent cells, thereby improving diseases caused by cellular aging and prolonging the lifespan of cells and completed the present invention.

The present invention may provide a senolytics composition comprising homoharringtonine as an active ingredient.

The senolytics may selectively kill senescent cells.

The senescent cells may be selected from the group consisting of fibroblasts and renal tubular epithelial cells, in which senescence is induced by drug treatment or subculture.

The present invention may comprise homoharringtonine as an active ingredient, and the homoharringtonine can provide a reagent composition for senolytics which kills senescent cells in vitro.

In addition, the present invention can provide a method of killing senescent cells comprising treating homoharringtonine on fibroblasts or renal tubular epithelial cells isolated from mammals other than humans in vitro.

The present invention can provide a senomorphics composition comprising homoharringtonine as an active ingredient.

The senomorphics may restore the function of the senescent cells to normal cells.

The senescent cells may be selected from the group consisting of vascular endothelial cells, retinal pigmented epithelial cells, and melanocytes, which are induced senescence by drug treatment or subculture.

The present invention may comprise homoharringtonine as an active ingredient, and the homoharringtonine can provide a reagent composition for senomorphics which restores the function or morphology of senescent cells to normal cells in vitro.

In addition, the present invention can provide a method of restoring the function or morphology of senescent cells to normal cells, comprising treating homoharringtonine on vascular endothelial cells, retinal pigmented epithelial cells, or melanocytes isolated from mammals other than humans in vitro.

The present invention can provide a pharmaceutical composition for preventing or treating cellular senescence-associated diseases comprising homoharringtonine as an active ingredient.

The homoharringtonine may prevent or treat diseases induced by cellular aging by selectively killing senescent cells or restoring a function or morphology of the senescent cells to normal cells.

The cellular senescence-associated disease may be selected from the group consisting of tissue fibrosis, senile eye disease, atherosclerosis, osteoarthritis, degenerative brain disease, obesity, diabetes and chronic skin damage.

In more detail, the tissue fibrosis may be selected from the group consisting of renal fibrosis and peritoneal fibrosis, but it is not limited thereto.

The senile eye disease may be selected from the group consisting of cataract, glaucoma, and macular degeneration, but it is not limited thereto.

The degenerative brain disease may be selected from the group consisting of Parkinson's disease, Alzheimer's disease and stroke, but it is not limited thereto.

The present invention can provide a composition for whitening skin comprising homoharringtonine as an active ingredient.

The homoharringtonine may inhibit the proliferation of aging-induced melanocytes.

The skin whitening composition may be provided as a pharmaceutical composition, health food or cosmetic composition.

In one embodiment of the present invention, the pharmaceutical composition comprising homoharringtonine as an active ingredient may be used as any one formulation selected from the group consisting injections, granules, powders, tablets, pills, capsules, suppositories, gels, suspensions, emulsions, drops or solutions according to the conventional method.

In another embodiment of the present invention, the pharmaceutical composition comprising homoharringtonine as an active ingredient may further comprise at least one additive selected from the group consisting of carriers, excipients, disintegrants, sweeteners, coating agents, swelling agents, lubricants, slip modifiers, flavors, antioxidants, buffers, bacteristats, diluents, dispersants, surfactants, binders and lubricants, which are conventionally used for the preparation of the pharmaceutical composition.

Specifically, examples of the carrier, excipient and diluent include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oil. Solid formulations for oral administration include tablets, pills, powders, granules, capsules, etc., and such solid formulations may contain at least one excipient such as starch, calcium carbonate, sucrose or lactose, gelatin and the like in addition to the composition. Furthermore, in addition to simple excipients, lubricants such as magnesium stearate and talc are also used. Examples of the liquid formulations for oral administration include suspensions, solutions, emulsions, syrups and the like, and various excipients such as wetting agents, sweeteners, fragrances, preservatives and the like may be included in addition to water and liquid paraffin which are commonly used as simple diluents. Formulations for parenteral administration include sterile aqueous solutions, non-aqueous solutions, suspensions, emulsions, freeze-dried preparations, suppositories and the like. Examples of the non-aqueous solution and the suspension include propylene glycol, polyethylene glycol, vegetable oil such as olive oil, injectable ester such as ethyl oleate, and the like. As the base of the suppository, witepsol, macrogol, tween 61, cacao butter, laurinum, glycerogelatin and the like can be used.

According to one embodiment of the invention, the pharmaceutical composition may be administered intravenously, intraarterially, intraperitoneally, intramuscularly, intrasternally, transdermally, nasally, inhaled, topically, rectally, orally, intraocularlly or intradermally to the subject in the conventional manner.

The preferred dosage of homoharringtonine may vary depending on the condition and weight of the subject, the type and extent of the disease, the drug form, the route of administration, and the duration, and may be appropriately selected by those skilled in the art. According to one embodiment of the present invention, the daily dosage may be, but is not limited to, 0.01 to 200 mg/kg, specifically 0.1 to 200 mg/kg, more specifically 0.1 to 100 mg/kg. Administration may be administered once a day or divided into several times, and the scope of the invention is not limited thereto.

In the present invention, the 'subject' may be a mammal including a human, but it is not limited thereto.

In another embodiment of the present invention, the health food may be used with other foods or food additives in addition to homoharringtonine, and may be appropriately used according to the conventional method. The mixed amount of the active ingredient may be appropriately determined depending on the purpose of use thereof, for example, prophylactic, health or therapeutic treatment.

The effective dose of the compound contained in the health food composition may be used in accordance with the effective dose of the therapeutic agent, but in the case of prolonged intake for the purpose of health and hygiene or health control, it may be less than the above range and since the active ingredient has no problem in terms of safety, it is evident that the active ingredient may be used in an amount above the above range.

There is no particular limitation on the kind of the health food, for example, meat, sausage, bread, chocolate, candy, snacks, confectionery, pizza, ramen, other noodles, gums, dairy products including ice cream, various soups, beverages, tea, drinks, alcoholic drinks, vitamin complexes, etc.

In another embodiment of the present invention, the cosmetic composition may include a stabilizer, a solubilizing agent, vitamins, pigments, and conventional adjuvants such as a flavoring agent, and a carrier in addition to homoharringtonine, which is an active ingredient.

The cosmetic composition may be prepared in any formulation conventionally prepared in the art, for example, solution, suspension, emulsion, paste, gel, cream, lotion, powder, oil, powder foundation, emulsion foundation, wax foundation or spray, but it is not limited thereto. More specifically, it may be prepared in the formulation of a sun cream, a skin softener, an astringent lotion, a nutritional lotion, a nutritional cream, a massage cream, an essence, an eye cream, a pack, a spray or a powder.

When the formulation of the present invention is a paste, cream or gel, animal oil, vegetable oil, wax, paraffin, starch, tragacanth, cellulose derivative, polyethylene glycol, silicone, bentonite, silica, talc, or zinc oxide may be used as carrier components.

When the formulation of the present invention is a powder or spray, lactose, talc, silica, aluminum hydroxide, calcium silicate or polyamide powder may be used as a carrier component, and in particular, in the case of a spray, a propellant such as chlorofluorohydrocarbon, propane/butane or dimethyl ether may be additionally included.

When the formulation is a solution or emulsion, a solvent, a solubilizing agent or an emulsifying agent is used as a carrier component, such as water, ethanol, isopropanol, ethyl carbonate, ethyl acetate, benzyl alcohol, benzyl benzoate, propylene glycol, 1,3-butyl glycol oil, glycerol aliphatic ester, polyethylene glycol or fatty acid ester of sorbitan.

When the formulation of the present invention is a suspension, liquid diluents such as water, ethanol or propylene glycol, suspending agents such as ethoxylated isostearyl alcohol, polyoxyethylene sorbitol ester and polyoxyethylene sorbitan ester, microcrystalline cellulose, aluminum metahydroxide, bentonite, agar or tragacanth, and the like may be used as carrier components.

In addition, the present invention can provide a composition for improving aging or extending life, comprising homoharringtonine as an active ingredient.

Hereinafter, the present invention will be described in more detail through examples. These examples are only intended to illustrate the present invention in more detail, and it will be apparent to those skilled in the art that the scope of the present invention is not limited by these examples according to the gist of the present invention. The examples of the present invention are provided to more completely explain the present invention to those of ordinary skill in the art.

The following experimental examples are intended to provide experimental examples commonly applied to each of the examples according to the present invention.

<Experimental Example 1> Cell Culture

Human dermal fibroblast (HDF) and human umbilical vascular endothelial cells (HUVEC) were purchased from LONZA Inc. In (Walkersville, MD), human epidermis melanocytes (HEM) were purchased from Cascade Biologics (Portland, OR, USA), and human retinal pigmented epithelial cells (ARPE-19) and HK2 cells (human tubular epithelial cells) were purchased from ATCC (Manassas, VA), respectively and used.

Human fibroblasts were cultured in DMEM (Dulbecco's Modified Eagle Medium) culture solution containing 10% fetal bovine serum (FBS), human umbilical vascular endothelial cells were cultured in EGM-2 culture solution, human epithelial melanocytes were cultured in M254 culture solution containing melanocyte growth factor (HMGS), human retinal pigmented epithelial cells were cultured in DMEM:F12 culture solution containing 10% FBS, and HK-2 cells were cultured in RPM11640 culture solution containing 10% FBS.

Cells ($2\times10^5$) were dispensed into a 100 mm culture dish and subcultured in a 37° C., 5% $CO_2$ incubator. When the cells grew to 80-90% in the culture dish, the cells were separated from the culture dish by treatment with a trypsin-EDTA solution, and the number of cells was measured.

The degree of cell growth was confirmed by the cell population doubling time (PDT) as shown in the following equation.

$PDT=((T-T_0)\log 2)/(\log N-\log N_0)$ (N=number of cells grown in the culture dish, $N_0$=number of first dispensed cells, $T-T_0$=cell culture time)

<Experimental Example 2> Preparation of Premature Senescent Cells by Treatment With Doxorubicin Each cell was treated in a serum-free culture solution containing doxorubicin (0.5 µM) for 4 hours. After washing the cells with a serum-free culture solution, the cells were cultured for 4 days in a culture solution containing 10% FBS, and then cellular aging was confirmed by measuring the level of senescence by staining with senescence-associated beta galactosidase.

<Experimental Example 3> Preparation of Replicative Senescent Cells

After dispensing $2\times10^5$ cells in a 100 mm culture dish, they were cultured in a 37° C., 5% $CO_2$ incubator. When the cells grew to 80-90% in the culture dish, the cells were removed by treatment with trypsin-EDTA, and the number of cells was measured, and the cell population doubling time (PDT) was measured.

By successively subculturing the cells in the same process as described above, replication aging was induced. PDT of young fibroblasts was 36 hours, PDT of replicative senescent fibroblasts was 12 days, PDT of young vascular endothelial cells was 24 hours, and PDT of replicative senescent vascular endothelial cells was 7 days, PDT of young human melanocytes was 2 days, and PDT of replicative senescent human melanocytes was 20 days.

The level of cellular senescence was confirmed by staining of senescence-associated beta galactosidase and analysis of p53 and p16 protein expressions.

<Experimental Example 4> Confirmation of Effective Substances of Senolytics and Senomorphics From Clinical Test Compounds 2,150 clinical trial compounds were distributed from Korea Chemical Bank.

Human fibroblasts and human vascular endothelial cells, in which premature senescence was induced by treatment with doxorubicin were dispensed into a 96-well plate, and then 2,150 compounds were treated at a concentration of 100 nM for 4 days, respectively. The degree of survival of senescent cells was investigated by CCK-8 analysis, and the degree of senescence of cells was investigated by senescence-associated beta galactosidase staining.

<Experimental Example 5> Drug Treatment

Homoharringtonine was purchased from TOCRIS Bioscience (Minneapolis, MN, USA), rapamycin was purchased from EMD Millipore (Burlington, MA, USA), and ABT263 was purchased from Selleckchem (Houston, TX, USA).

After each sample was dissolved in DMSO, young cells, replicative senescent cells, and premature senescent cells treated with doxorubicin were treated with 100 nM homoharringtonine, 100 nM rapamycin, 100 nM ABT263, respectively. After incubation for 4 days in a 37° C., 5% $CO_2$ incubator, the degree of cell survival was confirmed by CCK-8 analysis, the degree of cellular aging was confirmed by senescence-related beta-galactosidase (SAβG) staining, p53 and p16 protein expression analysis, and apoptosis was confirmed by analysis of PARP and caspase-3 protein expression.

<Experimental Example 6> Analysis of Senescence-Associated β-Galactosidase (SAβG) Staining The cells were washed with 1×phosphate buffer solution, and fixed with a phosphate buffer solution containing 3.7% (v/v) paraformaldehyde. After adding 1 mg/ml 5-bromo-4-chloro-3-indolyl-β-D-galactoside, 40 mM citric acid-sodium phosphate (pH 6.0), 5 mM potassium ferricyanide, 5 mM potassium ferrocyanide, 150 mM NaCl, and 2 mM $MgCl_2$ solution, it was reacted at 37° C. for 18 hours. It was stained with eosin as a control stain. Cells stained blue in the cytoplasm were identified using an optical microscope.

<Experimental Example 7> Cell Survival Analysis (Cell Counting Kit-8 Assay; CCK-8)

Young cells ($1\times10^3$ cells/well) or senescent cells ($2\times10^3$ cells/well) were dispensed into a 96-well plate, and cultured overnight in a 37° C., 5% $CO_2$ incubator.

Homoharringtonine, ABT263 and rapamycin were treated at each concentration, and then incubated for 4 days in a 37° C., 5% $CO_2$ incubator. 10 μl of CCK-8 reagent (Dojindo Molecular Technologies Inc., Kumamoto, Japan) was added to each well, and incubated for 2 hours in an incubator. Then, the absorbance was measured at 450 nm using a Microplate reader. The degree of cell survival was expressed as a relative value for the absorbance of the control group treated with only DMSO as 100%.

<Experimental Example 8> Lactate Dehydrogenase Assay (LDH)

Cytotoxicity against young and senescent cells was investigated with a lactate dehydrogenase (LDH) activity kit (Dojindo Molecular Technologies Inc.). Young cells ($1\times10^3$ cells/100 μl/well) or senescent cells ($2\times10^3$ cells/100 μl/well) were dispensed into a 96-well plate, and then cultured overnight in a 37° C., 5% $CO_2$ incubator.

Homoharringtonine, ABT263 and rapamycin were treated at each concentration, and then incubated for 4 days in a 37° C., 5% $CO_2$ incubator. After transferring the cell culture solution to a 1.5 ml tube, it was centrifuged at 4° C. and 12,000 rpm. 100 μl of the supernatant was dispensed into a 96-well plate, and 100 μl of the LDH measurement solution was added to each well, followed by reaction in a $CO_2$ incubator for 30 minutes. 50 μl of the LDH reaction stop solution was added, and absorbance was measured at 490 nm using a microplate reader. The level of LDH activity was expressed as a relative value based on the absorbance of the control group treated with only DMSO.

<Experimental Example 9> Preparation of Ischemia-Reperfusion Injury Induced Experimental Animal Animal experiments were performed with the approval of the Animal Experimental Ethics Committee, Yeungnam University College of Medicine (YUMC-AEC2018-024). C57BL/6J 8-week-old male mice were anesthetized by intraperitoneal injection of 2.5% Avertin (0.025 ml/g body weight). The mouse was placed on a hot plate at 37° C., and the left flank was incised to expose the left kidney. The renal arteriovenous blood vessels were ligated with a microaneurism clamp (Roboz), and whether the blood vessels were blocked or not was confirmed by the color of the kidneys. During the induction of ischemia, the body temperature of the mice was maintained at 36.5-37.5° C. After 35 minutes, the clamp was removed and it was confirmed that reperfusion occurred.

As a control, renal arteriovenous vessels were not ligated, and the rest was performed in the same manner as above. From 4 days after ischemia-reperfusion injury, 2.5 μl of 10 mM homoharringtonine was diluted in 100 μl of phosphate buffer solution at intervals of 2 days and injected into the abdominal cavity 3 times (HHT group). The control group was a group that did not induce ischemia-reperfusion injury (Sham group) and an ischemia-reperfusion injury group (PBS) was used. Three mice were used for each group.

Figure 8A:
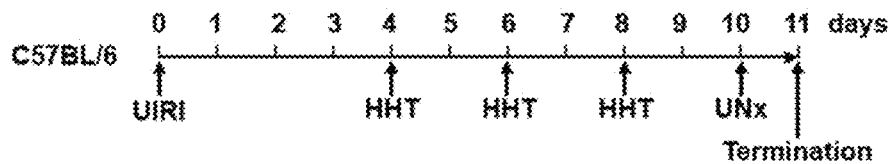
FIGS. 8A-8M show results of confirming the efficacy of homoharringtonine on renal fibrosis induced by renal ischemia-reperfusion injury in mice; A of FIG. 8A is a schematic diagram showing the experimental process.

The right kidney was removed on the 10th day of the ischemia-reperfusion injury and sacrificed on the 11th day (FIG. 8A). The left kidney in which ischemia-reperfusion injury was induced, was excised in half and fixed in 10% formalin solution or stored frozen in liquid nitrogen.

<Experimental Example 10> Evaluation of Kidney Function

In order to evaluate kidney function due to ischemia-reperfusion injury, creatinine and blood urea nitrogen (BUN) concentrations in plasma and urine were measured.

Blood was collected from the retro-orbital vascular plexus of the mouse using a heparin capillary tube, and plasma was separated. Plasma creatinine was measured by QuantiChrom™ creatinine assay kit (DICT-500; BioAssay Systems, Hayward, CA, USA), and BUN was investigated by measuring absorbance at 490 nm and 450 nm by a spectrophotometer, respectively by BUN colorimetric detection kit (Arbor Assays, Ann Arbor, Michigan, USA).

<Experimental Example 11> Confirmation of Malondialdehyde (MDA), Lipid Peroxides (Hydroperoxides) and Superoxides ($O_2-$)

To confirm the degree of lipid peroxidation in tissues, malondialdehyde (MDA) was confirmed by the TBARS method (Garcia Y J, et al., Journal of neuroscience methods. 2005).

Briefly, 1.4 ml of TBARS solution [0.375% thiobarbituric acid (TBA), 15% trichloroacetic acid (TCA), 0.25 N HCl] was added to the tissue pulverization solution (0.3 mg protein/0.1 ml), and boiled for 15 minutes at 95-100° C. and centrifugation was performed at 4° C. and 12,000 rpm for 10 minutes, and the absorbance of the supernatant was confirmed at 540 nm.

Lipid hydroperoxides were identified by ferrous ion oxidation xylenol orange (FOX) method (Jiang Z Y, et al., Lipids. 1991).

0.9 ml of FOX reagent (100 μM xylenol orange, 25 mM $H_2SO_4$, 0.1 M sorbitol, 2.5 mM ferrous ammonium sulfate] was reacted at room temperature for 30 minutes and then centrifuged to measure the absorbance of the supernatant at 570 nm.

Tissue superoxide was measured using dihydroethidium (DHE; Sigma, St. Louis, MO) (Peshavariya H M, et al., Free radical research. 2007). 0.2 ml of 10 μM DHE was added to 0.2 ml of the tissue pulverization solution and reacted at room temperature for 10 minutes. Fluorescence was measured at 37° C. with an Emax Precision Microplate Reader (Molecular Devices Corporation, Menlo Park, CA, USA) at 544 nm for excitation and 612 nm for emission.

<Experimental Example 12> Protein Extraction and Western Blot Analysis

After dispensing the cells into a 60 mm culture dish, the cells were cultured overnight in an incubator at 37° C. and 5% $CO_2$. After treatment with homoharringtonine, ABT263 and rapamycin, it was incubated for 3 days in a 37° C., 5% $CO_2$ incubator. After washing the cells with 1 xphosphate buffer, RIPA buffer (12 mM EDTA, 137 mM NaCl, 20 mM Tris-HCl (pH 8.0), 1 mM $Na_3VO_4$ (Sigma-Aldrich, USA) 10 mM NaF (Sigma), 1 mM PMSF (Sigma), 1% Triton X-100, 10% glycerol, protease inhibition cocktail (Roche, Germany)) was added and lysed.

The lysed cells were transferred to a 1.5 ml tube, pipetted 3-4 times, and then left on ice for 20 minutes. After centrifugation at 12,000 rpm for 20 minutes to recover the supernatant, the protein concentration of the supernatant was quantified by BCA analysis.

RIPA buffer was added to the tissue and pulverized with WiseTis homogenizer HG-15D (DAIHAN Scientific, Seoul, South Korea). Centrifugation was performed at 12,000 rpm at 4° C. for 20 minutes, and the supernatant was transferred to a new tube. The protein concentration of the supernatant was quantified by the BCA method.

After electrophoresis (SDS-PAGE) of 30 μg of protein, Western blot analysis was performed. After electrophoresis, the protein was transferred from the gel to a polyvinylidene fluoride membrane (Pall Corporation). The membrane was treated with a 5% Difco™ skim milk solution (Becton, Dickinson and Company, USA) for 2 hours at room temperature, and the primary antibody was added, followed by reaction at room temperature for 2 hours.

As the primary antibody, anti-p53 antibody, anti-p16 antibody, anti-caspase 3 antibody, anti-PARP antibody, anti-actin antibody, and anti-GAPDH antibody were purchased from Santa Cruz Biotechnology, Inc. Anti-phosphorylated-Rb antibody was obtained from New England Biolabs (Ipswich, MA, USA), and the anti-SOD2 antibody and anti-catalase antibody were obtained from Bioworld Technology Inc. (Louis Park, MN, USA), anti-4-HNE antibody, anti-α-smooth muscle actin antibody, and anti-type I collagen antibody were purchased from Abcam (Cambridge, UK). The membrane treated with the primary antibody was washed three times for 15 minutes each with TBST (20 mM Tris-HCl (pH 8.0), 137 mM NaCl, 0.1% Tween 20), and reacted for 60 minutes by treatment with the secondary antibody. After washing for at least 60 minutes with TBST, protein expression was confirmed using an ECL detection kit (Elpis Biotech, Daejeon, South Korea).

<Experimental Example 13> Preparation of Experimental Animal for Peritoneal Fibrosis For the production of peritoneal fibrosis experimental animals, a peritoneal fibrosis model by chlorhexidine gluconate (CHG) was used (Choi S Y, et al., Journal of dermatological science. 2018).

Figure 9A:
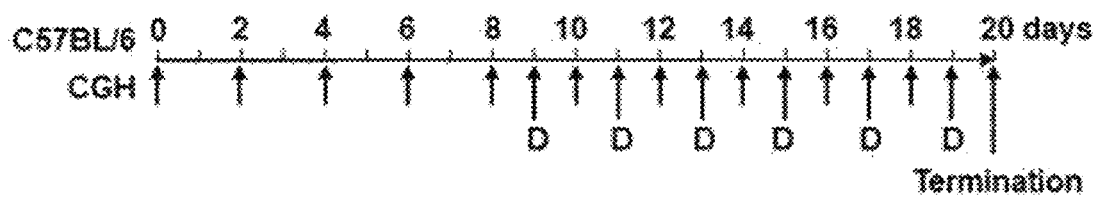
FIGS. 9A-9D show results of confirming the efficacy of homoharringtonine on peritoneal fibrosis caused by CHG in mice.
Figure 9B:
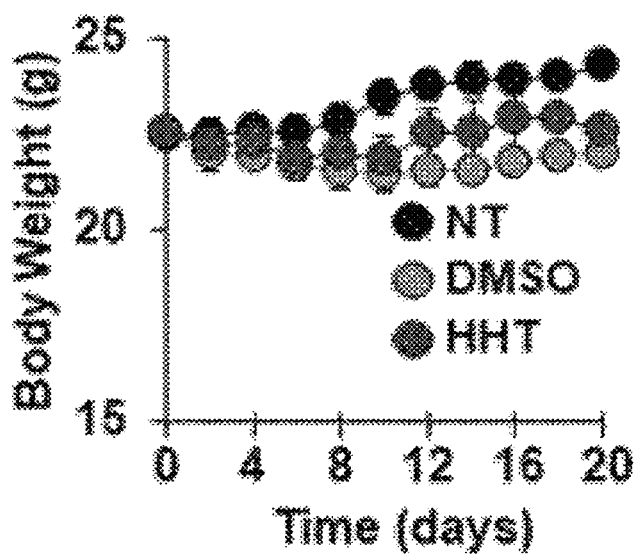

Referring to FIG. 9A, C57BL/6J 8-week-old male mice were intraperitoneally injected with a 0.1% CHG solution (0.1% CHG in a 15% ethanol phosphate buffer solution) at 10 ml/kg for 20 days at intervals of 2 days. From the 9th day, 2.5 μl of 10 mM homoharringtonine (HHT group) or 2.5 μl of DMSO (DMSO group) was diluted in 100 μl phosphate buffer solution and intraperitoneally injected at intervals of 2 days.

As a negative control (group NT), 100 μl of a 15% ethanol phosphate buffer solution was injected intraperitoneally instead of a 0.1% CHG solution. On the 20th day, the mice were sacrificed, the peritoneal tissue was excised, and the tissue was fixed in 4% paraformaldehyde solution.

<Experimental Example 14> Preparation and Staining of Tissue Samples

The tissue fixed in 10% formalin solution was embedded with paraffin and cut into 4 μm to prepare a tissue sample. After removing paraffin from the tissue sample, hematoxylin-eosin staining, trichrome staining, and PAS staining were performed.

The degree of fibrosis of the kidney was measured by analyzing the degree of collagen staining using the i-Solution™ software program (IMT Inc., Canada) after trichrome staining. The degree of cell senescence in tissue samples was investigated by staining lipofuscin with Sudan black B (Viegas M S, et al., European journal of histochemistry: EJH. 2007). The degree of peritoneal fibrosis was measured by measuring the submesothelial thickness of the peritoneal mesothelial cell layer using the NIH Image J program.

<Experimental Example 15> Statistical Analysis

Values are expressed as mean and standard error. The statistical significance of this study was reviewed by one-way ANOVA analysis and Turkey post hoc verification.

<EXAMPLE 1> CONFIRMATION OF SENOLYTICS ACTION OF HOMOHARRINGTONINE

1. Confirmation of Senolytics Action of Homoharringtonine on Human Fibroblasts

Human fibroblasts were treated with doxorubicin to induce early cellular senescence. Cells in which early senescence was induced were treated with 0.01% DMSO (NT), 100 nM homoharringtonine (HHT), 100 nM rapamycin (Rap) and 100 nM ABT263 (ABT), and 4 days later, SAβG activity staining was performed to confirm the degree of senescence of the cells, and the degree of cell survival was confirmed by performing CCK-8 analysis.

Rapamycin is a type of senomorphics known to inhibit cellular aging, and ABT263 is a type of senolyitics known to induce senescent cell-specific apoptosis, and the above two drugs were used as positive controls.

Figure 1B:
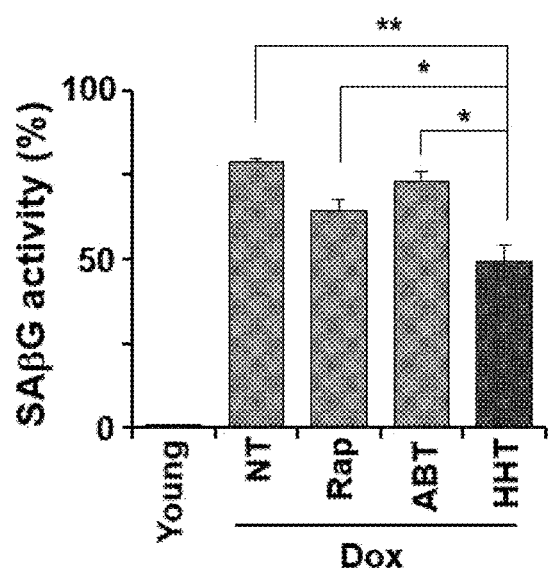
Figure 1C:
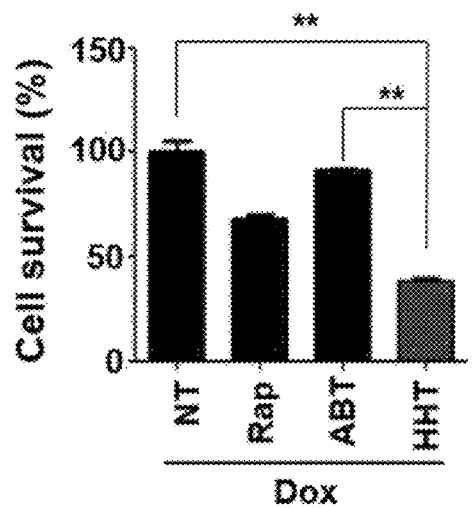

As a result of treatment of 100 nM homoharringtonine in human fibroblasts in which early cellular aging was induced by doxorubicin treatment, SAβG activity was significantly reduced compared to the DMSO-treated group as shown in FIG. 1A and FIG. 1B, and as shown in FIG. 1C, cell survival also decreased significantly ($p<0.01$). In addition, it was confirmed to be significantly reduced compared to those of rapamycin- and ABT263-treated experimental group.

From the above results, it was confirmed that the senolytics effect of homoharringtonine was more remarkable than that of rapamycin and ABT263.

In addition, it was confirmed whether homoharringtonine exhibits senescent cell-specific cytotoxicity in early aged human fibroblasts as well as replicative senescent human fibroblasts.

Figure 2A:
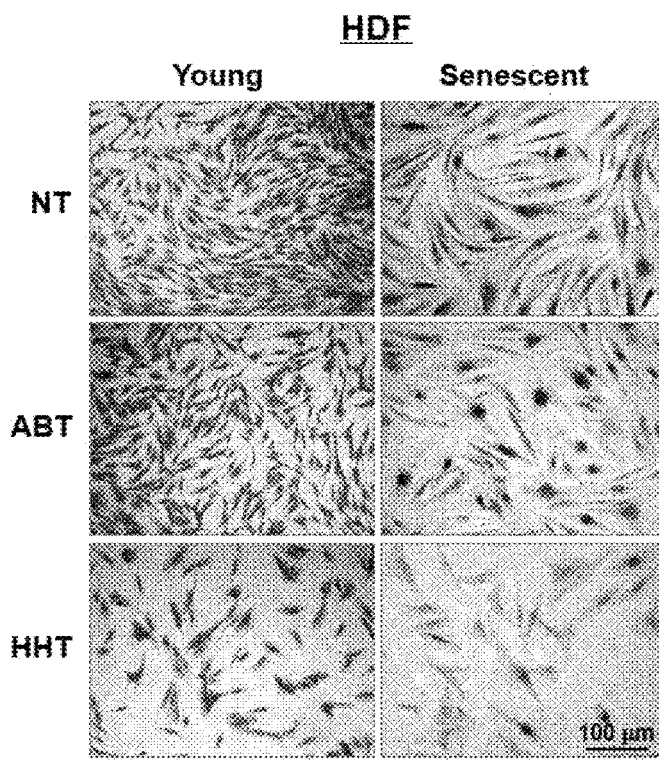
FIGS. 2A-2D show results of confirming the senolytics action of homoharringtonine in replicative senescent human fibroblasts.
Figure 2B:
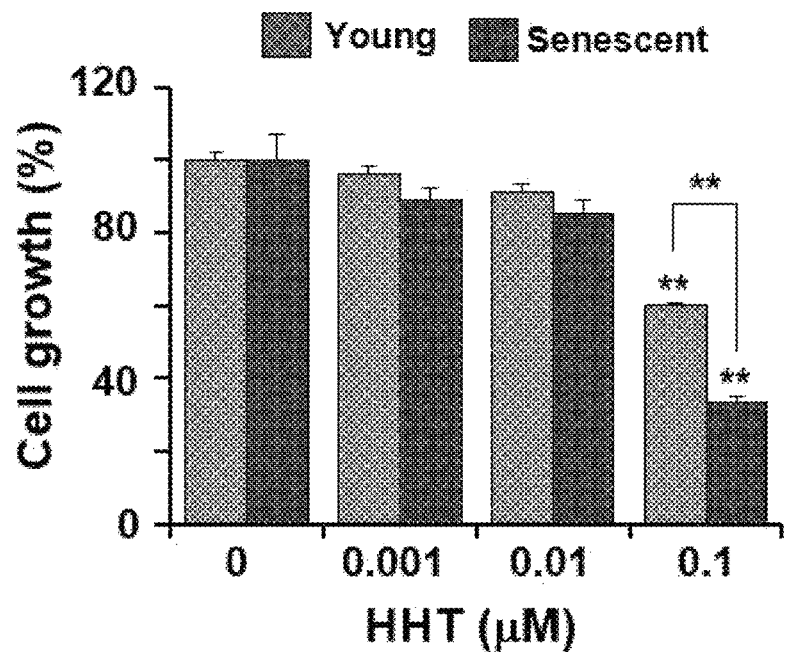

As a result, as shown in FIG. 2A and FIG. 2B, when the concentration of homoharringtonine was increased in the young fibroblasts and the replicative senescent fibroblasts, the cell growth was significantly decreased in the senescent cells compared to the young cells in a concentration-dependent manner.

From the above results, whether the cell growth inhibitory effect of homoharringtonine in senescent cells is due to cytotoxicity was investigated by LDH activity analysis.

Figure 2C:
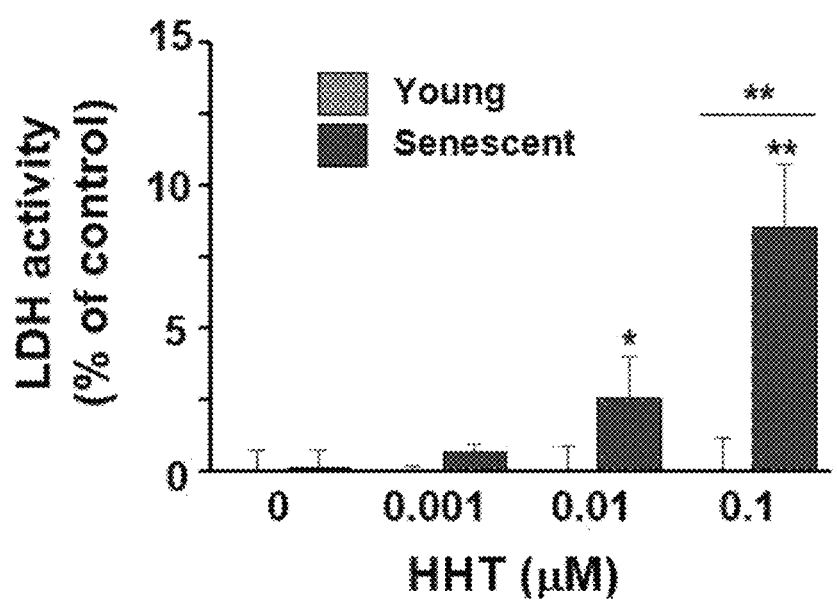

As a result, as shown in FIG. 2C, as it was confirmed that the LDH activity by homoharringtonine was increased only in replicative senescent cells compared to young cells, it was confirmed that homoharringtonine exhibited senescent cell-specific cytotoxicity.

On the other hand, in order to confirm the relationship between the cytotoxicity of homoharringtonine on replicative senescent human fibroblasts and apoptosis of senescent cells, expression of PARP and caspase-3 was confirmed by Western blot analysis.

Figure 2D:
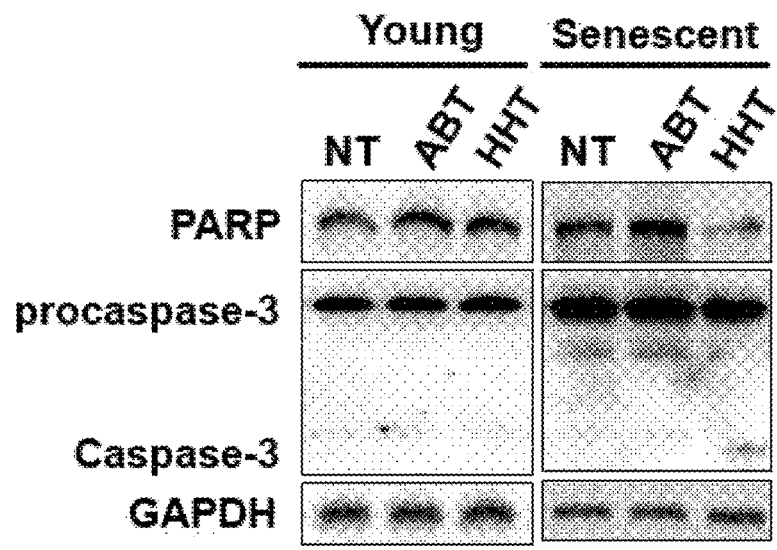

As a result, as shown in FIG. 2D, it was confirmed that PARP expression decreased and caspase-3 expression increased only in senescent cells by homoharringtonine treatment, and homoharringtonine induces senescent cell-specific apoptosis.

From the above results, homoharringtonine was identified as a drug that acts as a new senolytics agent that induces senescent cell-specific apoptosis in human fibroblasts.

2. Confirmation of Senolytics Action of Homoharringtonine in Human HK2 Cells

Human HK2 cells were treated with doxorubicin to induce early cellular aging, and then early aged cells were treated with 0.01% DMSO, 100 nM homoharringtonine, 100 nM rapamycin, and 100 nM ABT263, respectively, and after 4 days, SAβG staining was performed to confirm the degree of cellular aging, and the cell survival of the cells was confirmed by performing CCK-8 analysis.

Figure 3A:
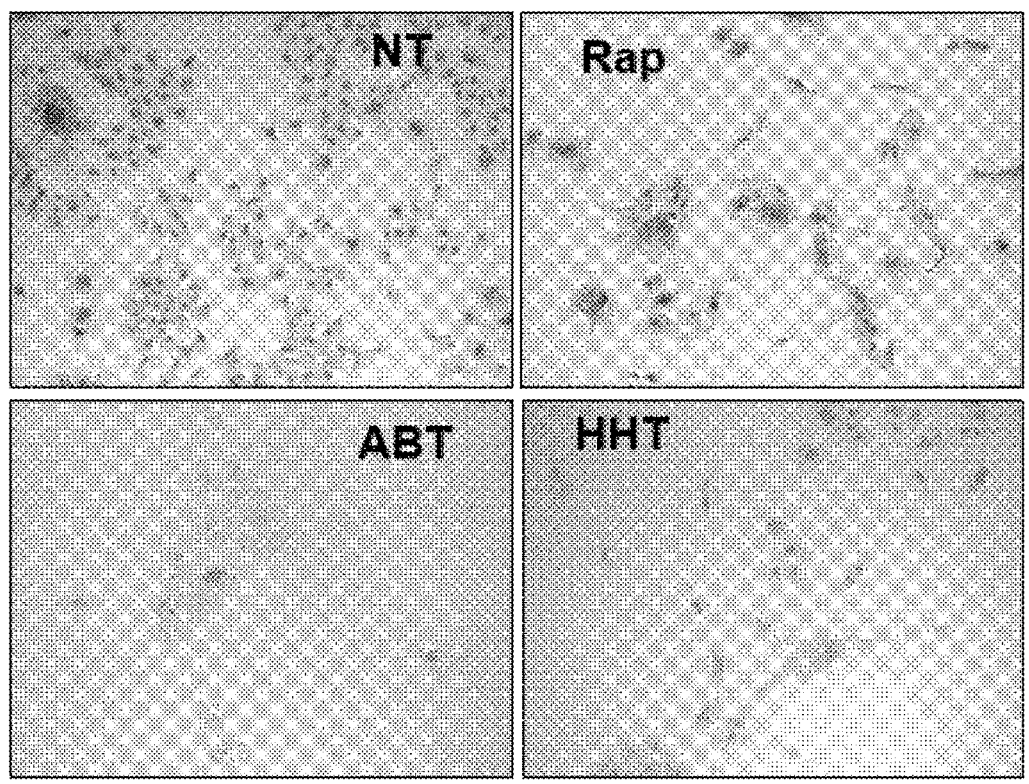
FIGS. 3A-3B show results of confirming the senolytics action of homoharringtonine in premature senescent renal tubular cells (HK2) by doxorubicin.
Figure 3B:
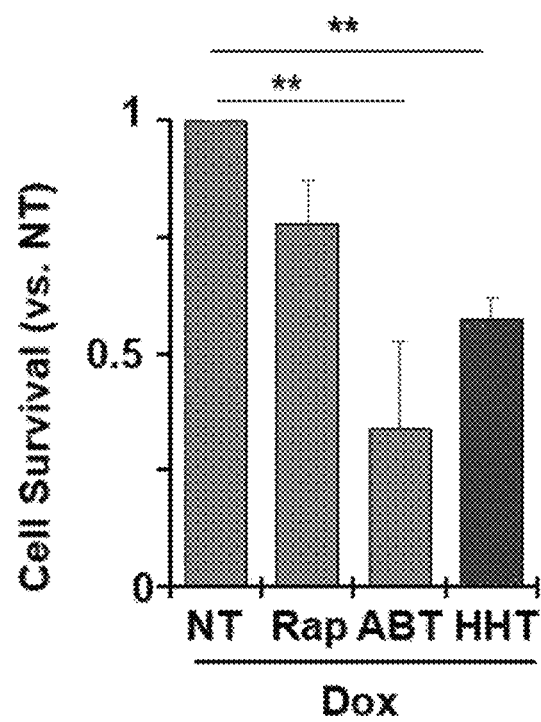

As a result, as shown in FIG. 3A and FIG. 3B, it was confirmed that the experimental group treated with homoharringtonine significantly reduced the survival of early aged HK2 cells compared to that of the DMSO-treated group ($p<0.01$).

From the above results, it was confirmed that homoharringtonine acts as senolytics in human HK2 cells.

<EXAMPLE 2> CONFIRMATION OF SENOMORPHICS ACTION OF HOMOHARRINGTONINE

1. Confirmation of Senomorphics Action of Homoharringtonine on Human Umbilical Vascular Endothelial Cells Human umbilical vascular endothelial cells were treated with doxorubicin to induce early cellular aging, and then early aged cells were treated with 0.01% DMSO, 100 nM homoharringtonine, 100 nM rapamycin and 100 nM ABT263, and after 4 days, SAβG staining was performed to confirm the degree of cellular aging, and the cell survival of the cells was confirmed by performing CCK-8 analysis.

Figure 4A:
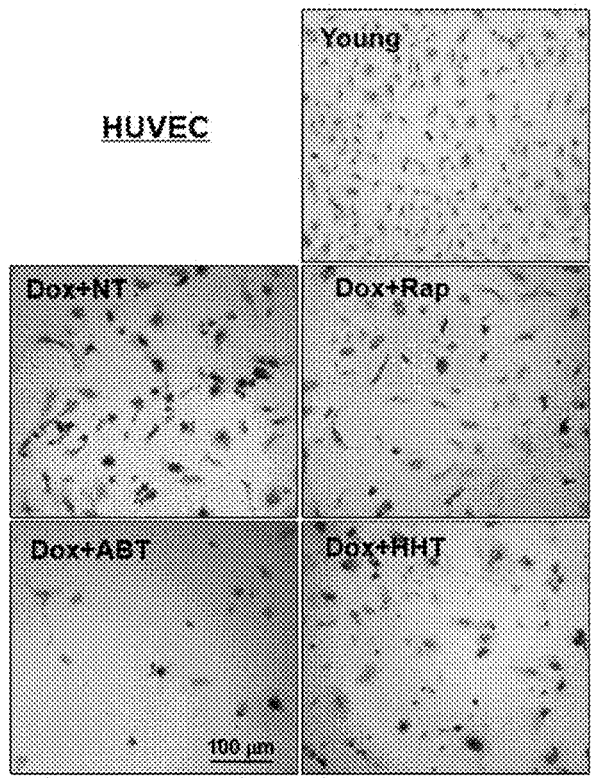
Figure 4B:
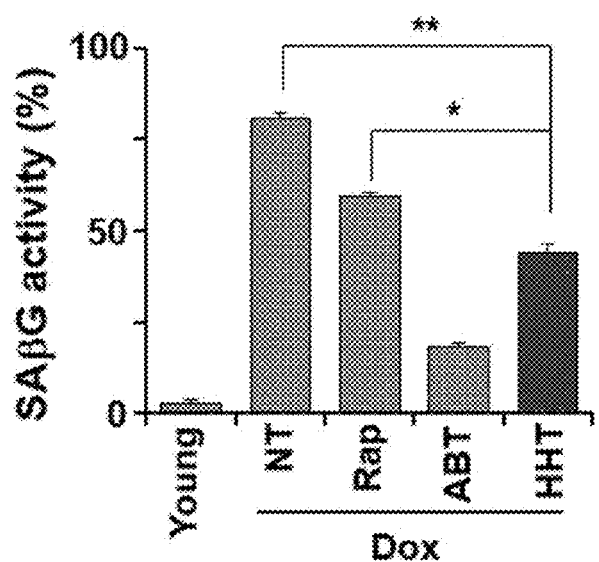

As a result, as shown in FIG. 4A and FIG. 4B, it was confirmed that the SAβG activity of the experimental group in which human vascular endothelial cells in which early cellular aging was induced by doxorubicin treatment was treated with 100 nM homoharringtonine was significantly decreased ($p<0.01$) compared to that of the DMSO-treated group and it was significantly decreased than that of rapamycin.

On the other hand, as shown in FIG. 4C, there was no difference in cell survival for early aged vascular endothelial cells compared to that of the DMSO-treated group.

From the above results, it was confirmed that homoharringtonine acts as a senomorphics capable of restoring the function and morphology of aged vascular endothelial cells to young cells.

On the other hand, it was confirmed whether homoharringtonine acts as a senomorphics in not only early aged cells but also replicative senescent vascular endothelial cells.

Figure 5A:
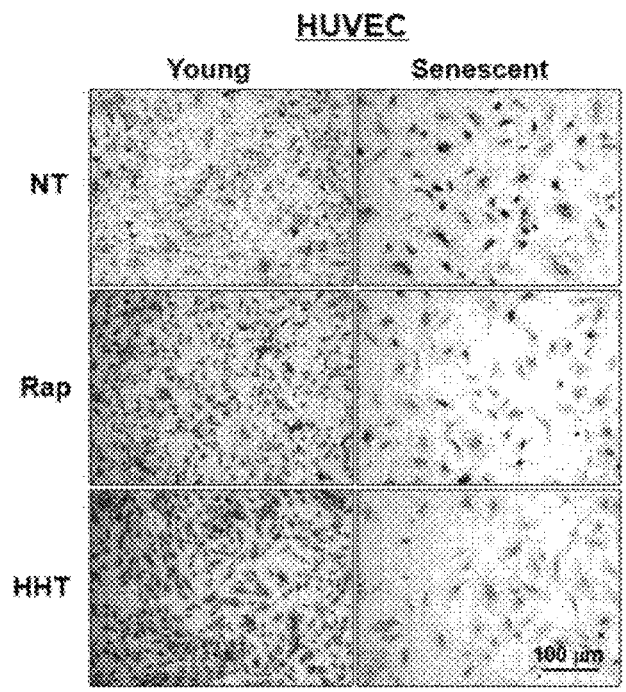
FIGS. 5A-5E show results of confirming the senomorphics action of homoharringtonine in replicative senescent vascular endothelial cells.
Figure 5B:
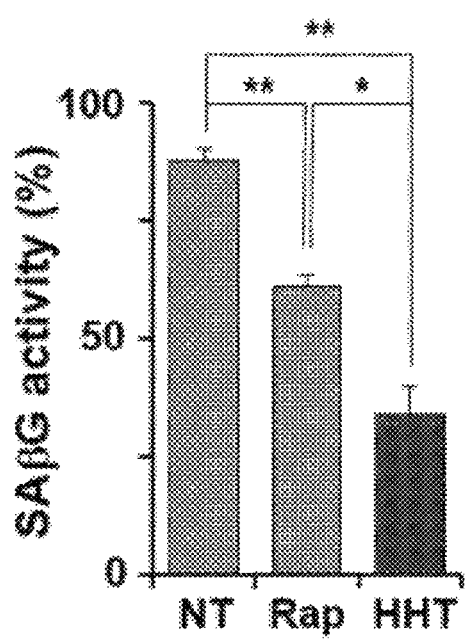
Figure 5C:
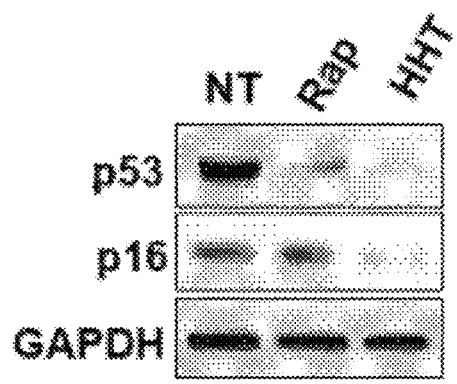
Figure 5D:
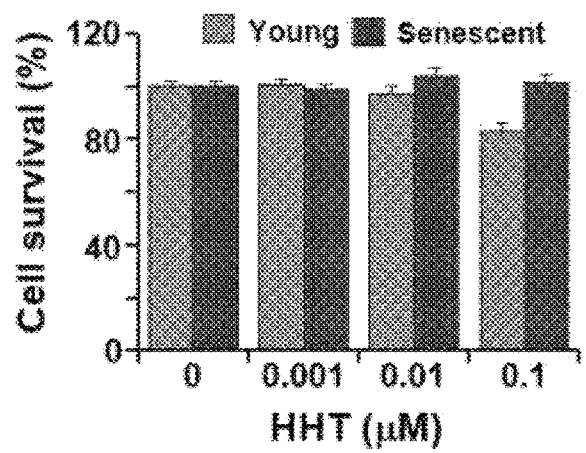
Figure 5E:
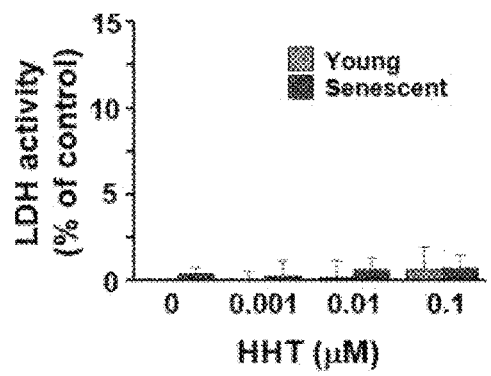

As a result, it was confirmed that SAβG activity was decreased in replicative senescent vascular endothelial cells by homoharringtonine treatment as shown in FIG. 5A to FIG. 5C, and expression of p53 and p16 proteins known to be increased in senescent cells was decreased. In addition, it was confirmed through CCK-8 analysis and LDH activity analysis as shown in FIG. 5D and FIG. 5E that homoharringtonine did not affect the cell survival of replicative senescent vascular endothelial cells, as in early aged cells.

From the above results, it was confirmed that homoharringtonine acts as a new senolytics capable of restoring the function and morphology of senescent cells to young cells in human vascular endothelial cells.

2. Confirmation of Senomorphics Action of Homoharringtonine on Human Retinal Pigmented Epithelial Cells Human retinal pigmented epithelial cells were treated with doxorubicin to induce early cellular aging, and then early aged cells were treated with 0.01% DMSO, 100 nM homoharringtonine, 100 nM rapamycin, and 100 nM ABT263, and 4 days later, SAβG staining was performed to confirm the cellular aging level and the degree of cell survival was confirmed by performing CCK-8 analysis.

Figure 6A:
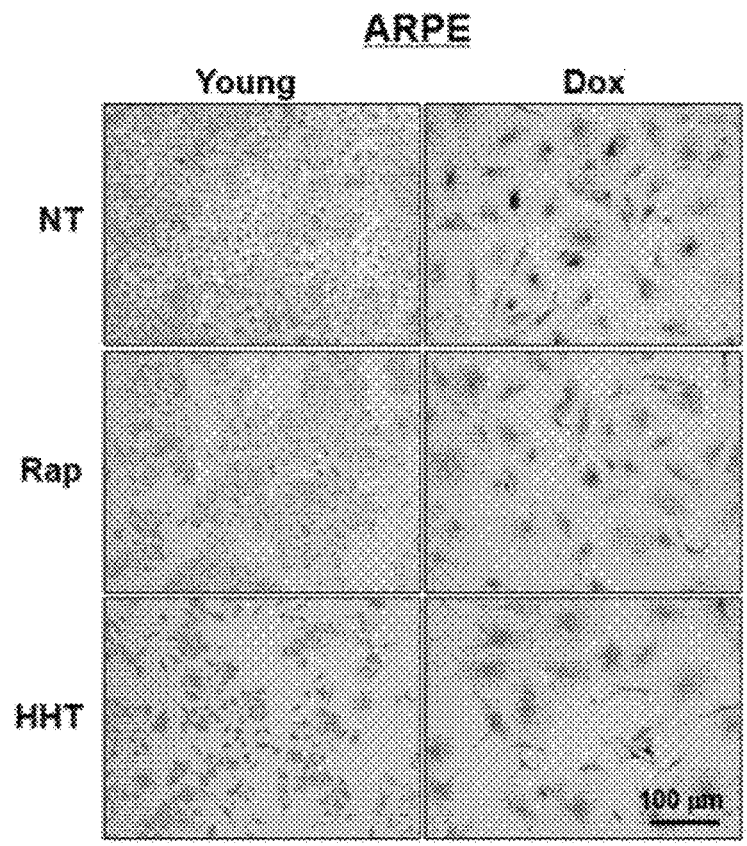
FIGS. 6A-6E show results of confirming the senomorphics action of homoharringtonine in premature senescent retinal pigmented epithelial cells (ARPE) by doxorubicin.
Figure 6B:
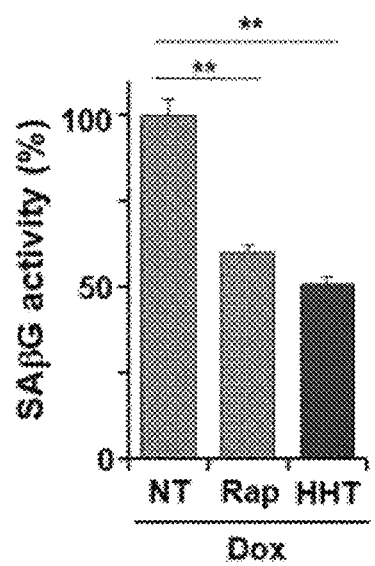
Figure 6C:
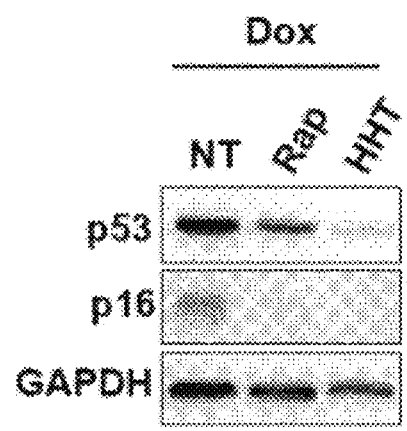

As a result, as shown in FIG. 6A and FIG. 6B, the SAβG activity staining of the experimental group in which human retinal pigmented epithelial cells induced with early cellular aging was treated with homoharringtonine significantly decreased ($p<0.01$) compared to that of the DMSO-treated group, and as shown in FIG. 6C, not only the SAβG activity, but also the expression of p53 and p16 proteins, which are known to be increased in senescent cells, was decreased.

Figure 6D:
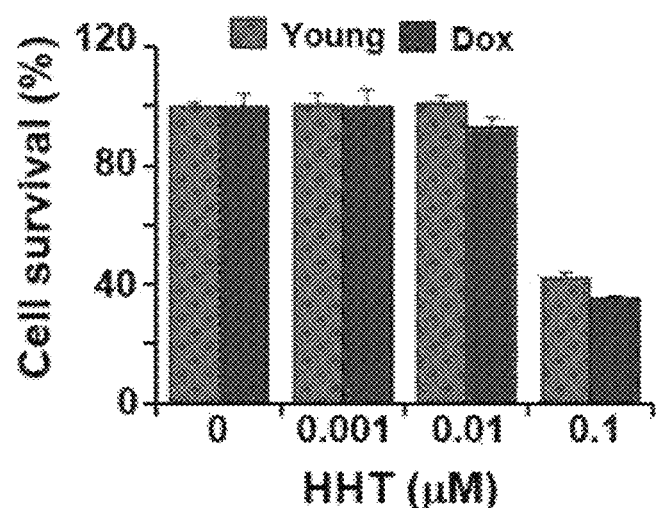
Figure 6E:
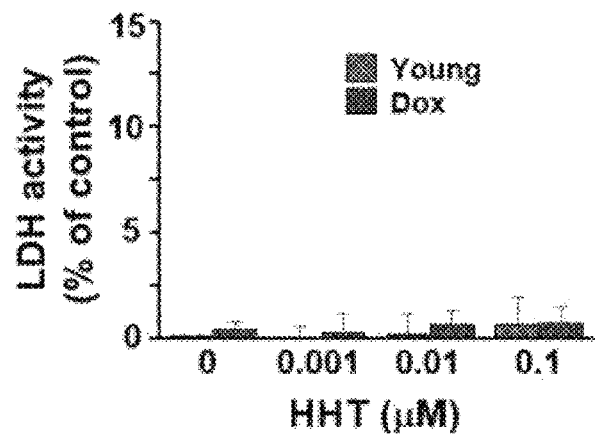

In addition, it was confirmed that senescent cell-specific cytotoxicity was not induced by homoharringtonine treatment through CCK-8 analysis and LDH activity analysis as shown in FIG. 6D and FIG. 6E.

From the above results, it was confirmed that homoharringtonine acts as a new senolytics capable of restoring the function and morphology of senescent cells into young cells in human retinal pigmented epithelial cells.

3. Confirmation of Senomorphics Action of Homoharringtonine in Human Epithelial Melanocytes Human melanocytes were subcultured 20 times to induce replication aging. Young cells and replicative senescent cells were treated with 0.01% DMSO, 100 nM homoharringtonine, and 100 nM rapamycin, respectively, and 4 days later, CCK-8 analysis was performed to confirm the degree of cell survival, and SAβG staining and cell morphology analysis were performed to confirm the degree of cellular aging.

As a result, as shown in FIG. 7A to FIG. 7D, the experimental group in which in the replicative senescent melanocytes was treated with 100 nM of homoharringtonine showed a significant decreased number of cells exhibiting SAβG activity staining and senescence-specific cell shape compared to those of the DMSO-treated group. In addition, it was confirmed that the senomorphics effect of homoharringtonine was more remarkable than that of rapamycin.

Figure 7A:
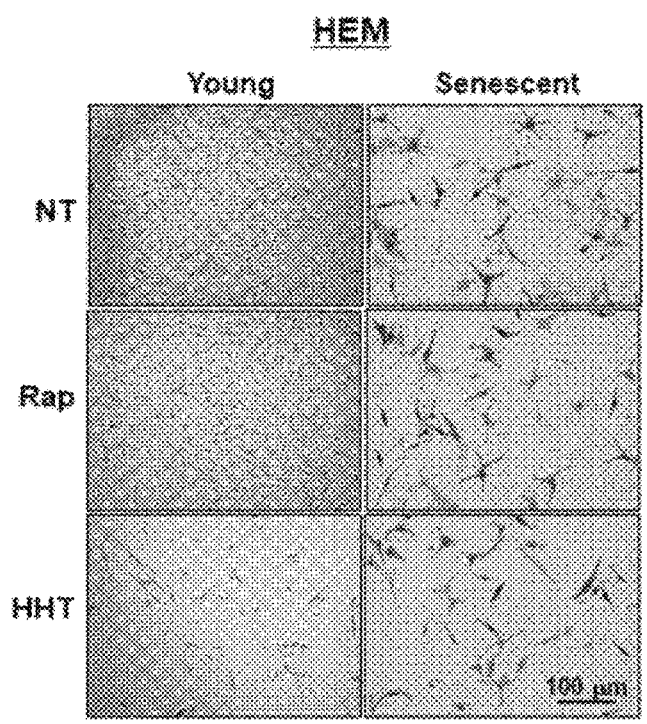
FIGS. 7A-7E show results of confirming the senomorphics action of homoharringtonine in replicative senescent melanocytes (HEM)
Figure 7B:
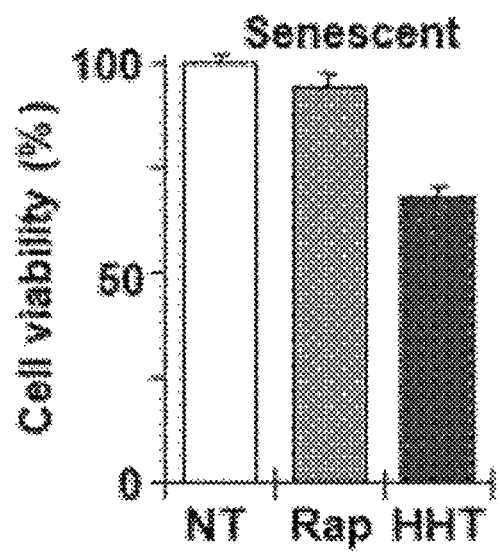
Figure 7C:
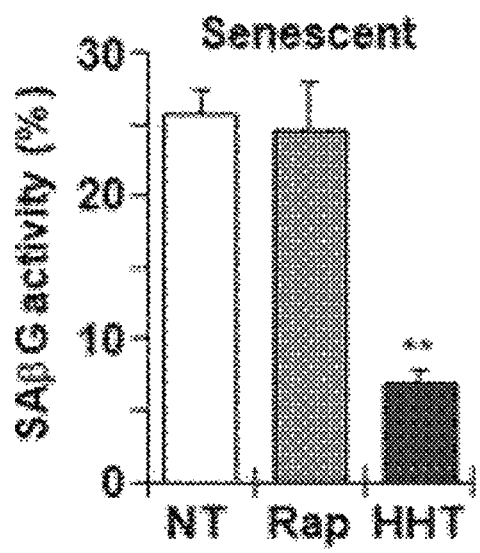
Figure 7D:
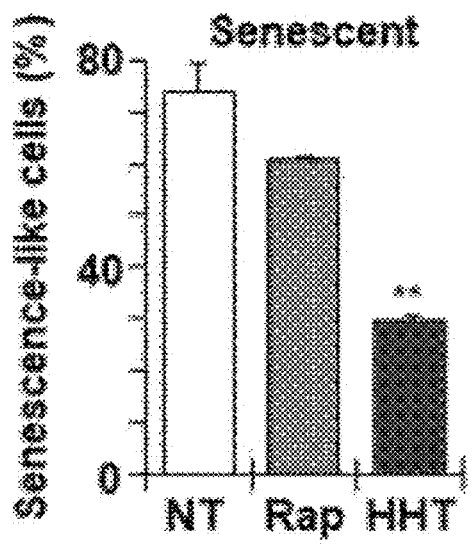
Figure 7E:
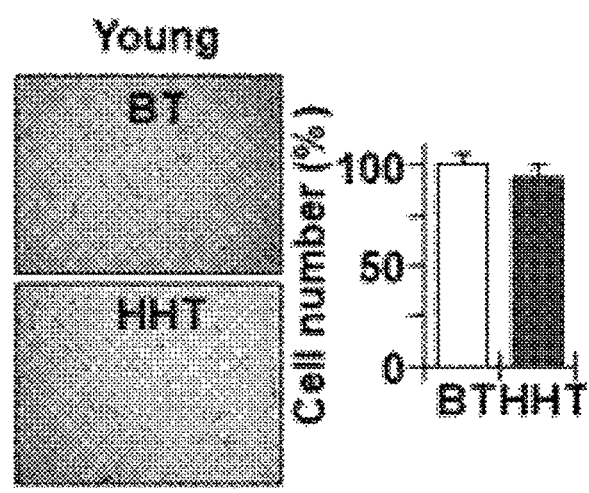

On the other hand, referring to FIG. 7A and FIG. 7E, when young melanocytes were treated with homoharringtonine, it was confirmed that cell proliferation was inhibited, and the proliferation inhibitory effect in young cells was determined by the number of cells before drug treatment (BT) and the number of cells after homoharringtonine treatment and there was no difference, and the above result was not a phenomenon caused by cell death.

From the above results, it was confirmed that homoharringtonine can act as a senolytics capable of restoring the function and morphology of senescent cells to young cells in melanocytes.

<EXAMPLE 3> CONFIRMATION OF EFFICACY OF HOMOHARRINGTONINE ON RENAL FIBROSIS INDUCED BY RENAL ISCHEMIA-REPERFUSION INJURY

As renal fibrosis induced by renal ischemia-reperfusion injury is reported to be related to the cellular aging of the tissue, the left renal blood vessels of mice were ligated and released for 35 minutes to induce ischemia-reperfusion injury.

After 4 days, 2.5 μl of 10 mM homoharringtonine was diluted in 100 μl phosphate buffer solution at intervals of 2 days and injected intraperitoneally 3 times (HHT group), a group that did not induce ischemia-reperfusion injury (Sham group) and an ischemia-reperfusion injury group (PBS) were designated as a control group, and the right kidney was removed on the 10th day of the ischemia-reperfusion injury, and sacrificed on the 11th day as shown in FIG. 8A, and the body weight before the ischemia-reperfusion injury and the body weight change on the 11th day were investigated.

Figure 8B:
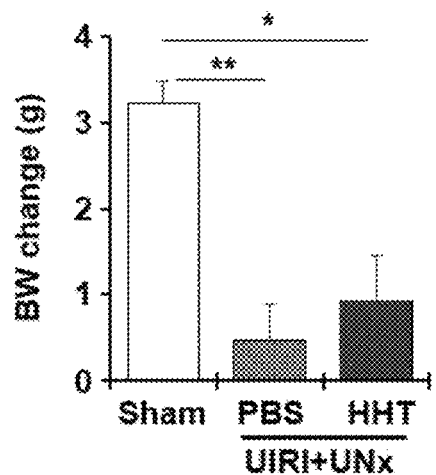

As a result, as shown in FIG. 8B, the weight gain of the PBS-treated group or the HHT-treated group was significantly reduced compared to the Sham group. However, it was confirmed that the HHT group increased body weight compared to the PBS group.

Figure 8C:
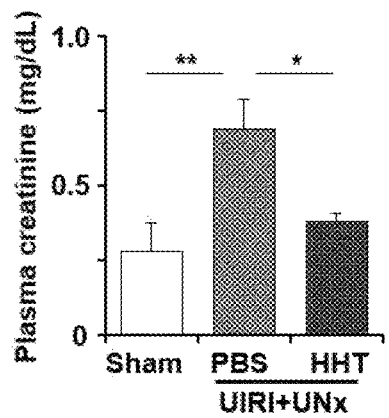
Figure 8D:
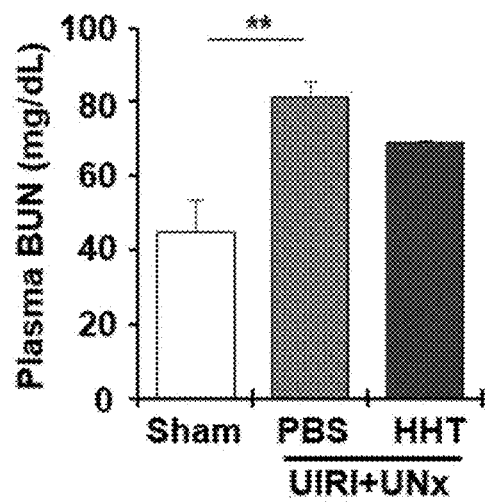
Figure 8E:
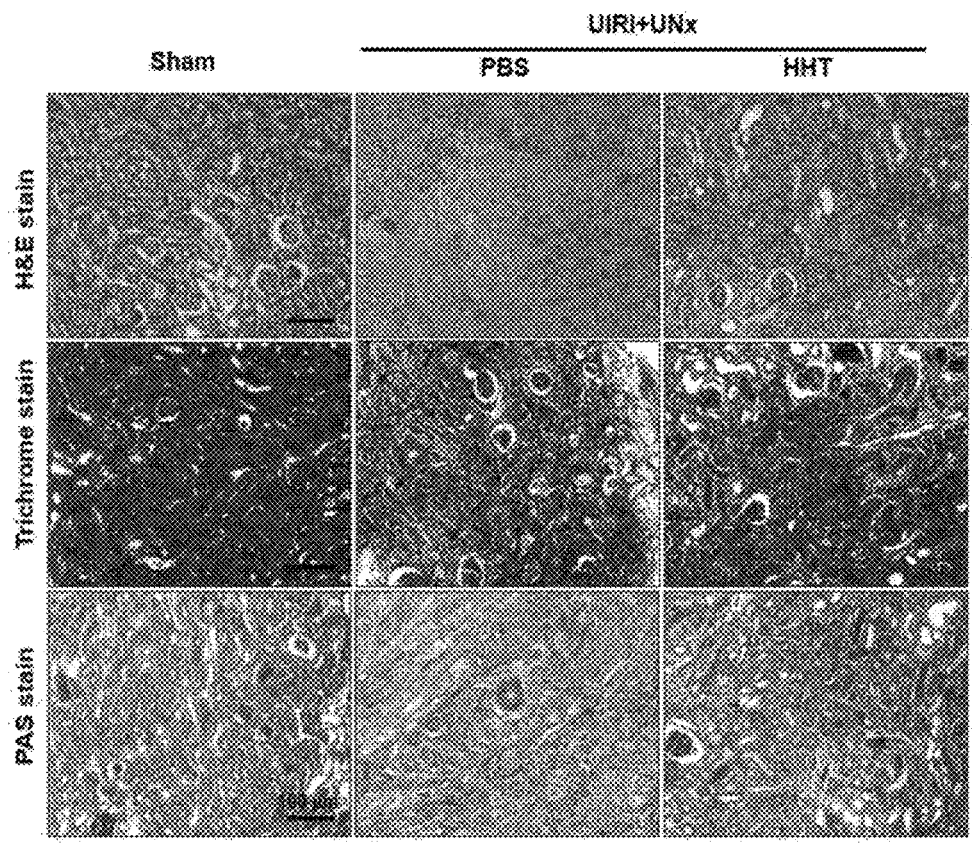
Figure 8F:
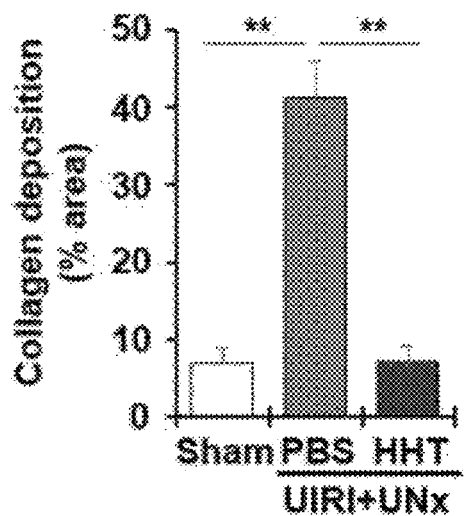

In addition, as shown in FIG. 8C and FIG. 8D, plasma creatinine and BUN were found to be decreased in the HHT-treated group compared to the PBS group, and as a result of renal tissue specimen examination, as shown in FIG. 8E and FIG. 8F, the damage to the renal tubules in the HHT group was significantly reduced compared to that in the PBS group, and the trichrome staining result showed that the degree of tissue fibrosis in the HHT group was significantly decreased compared to that in the PBS group.

On the other hand, when cellular aging occurs in tissues, lipofuscin is known to increase, and as it is reported that cellular aging can be measured enough to replace SAβG staining, lipofuscin in tissues was confirmed by staining with Sudan Black B.

Figure 8G:
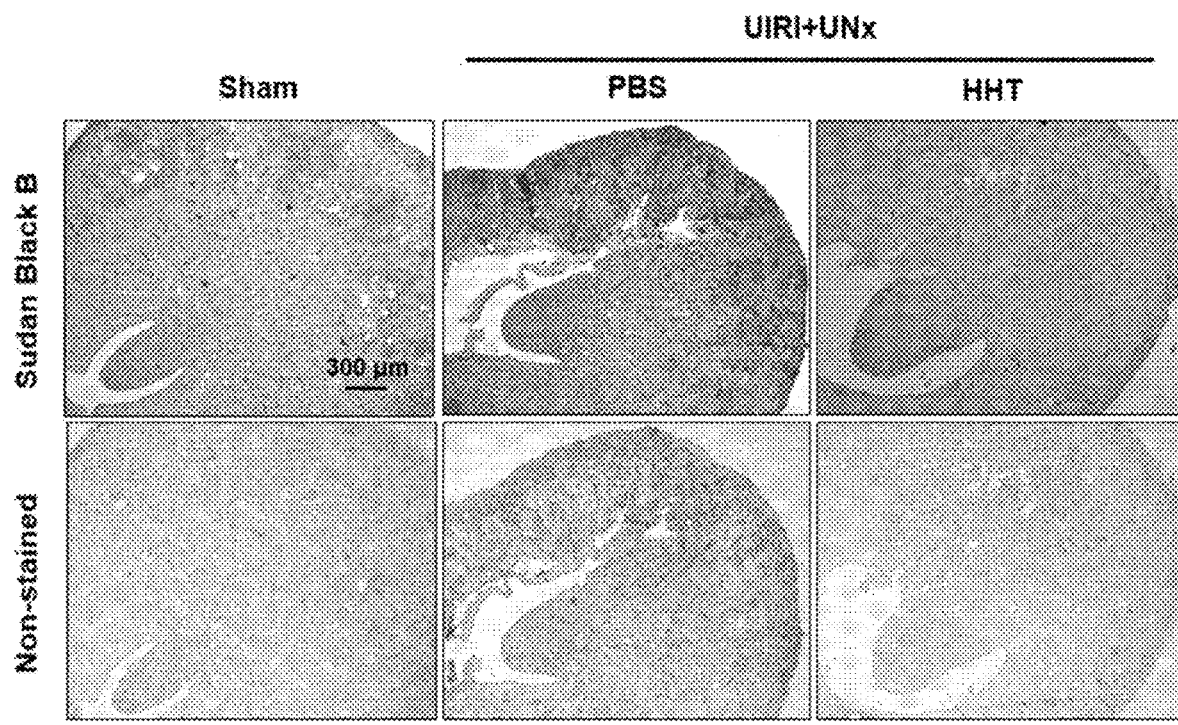

As a result, it was confirmed that the staining intensity of the HHT group was decreased compared to that of the PBS group, as shown in FIG. 8G.

Figure 8H:
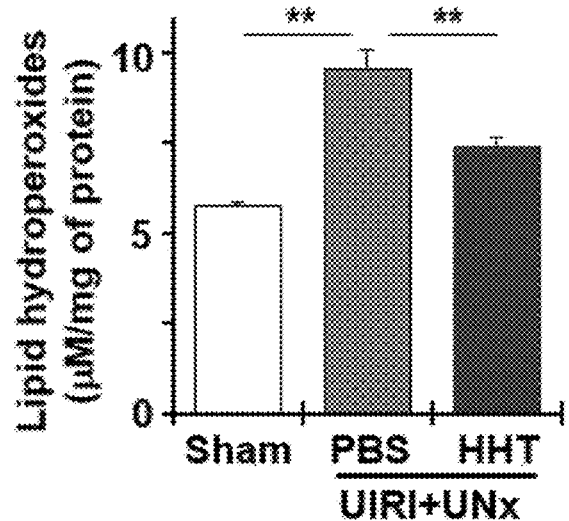
Figure 8I:
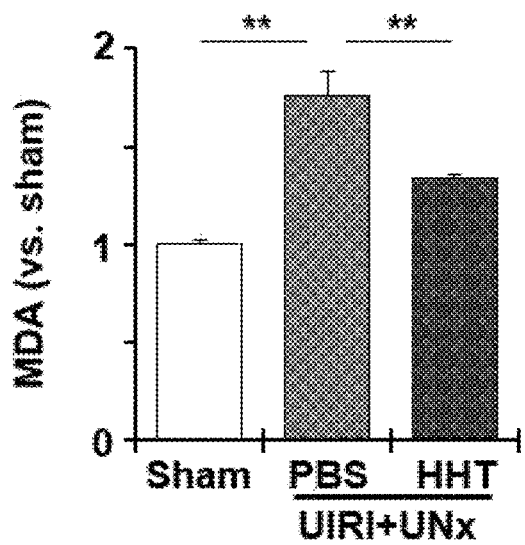
Figure 8J:
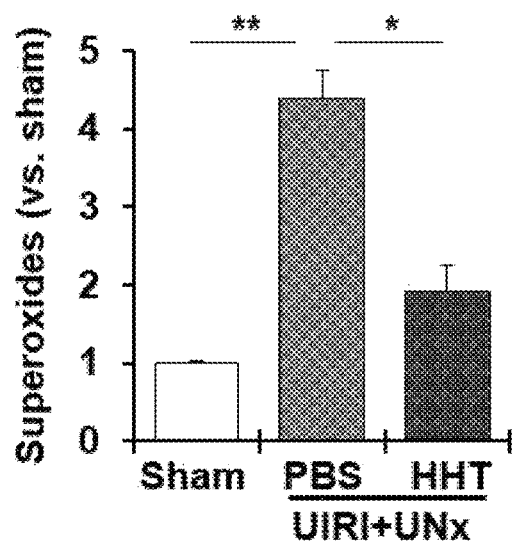

In addition, as a result of measuring the degree of oxidation of lipids by pulverizing the tissues with lipid hydroperoxides and MDA, it was confirmed that the degree of lipid oxidation in the HHT group was significantly reduced compared to that in the PBS group as shown in FIG. 8H and FIG. 8I and as shown in FIG. 8J, superoxides, a kind of reactive oxygen species, were also significantly reduced in the HHT group than in the PBS group.

Figure 8K:
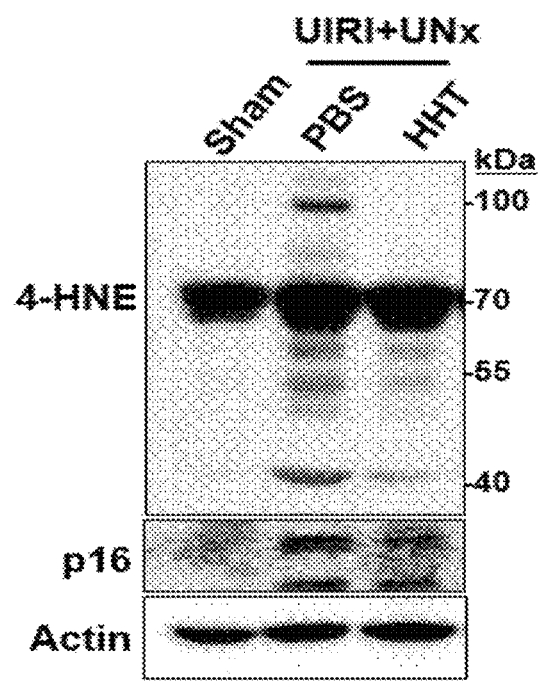
Figure 8L:
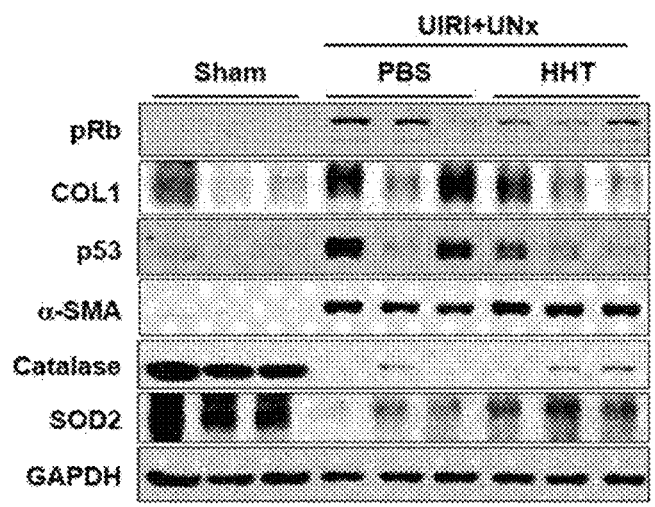
Figure 8M:
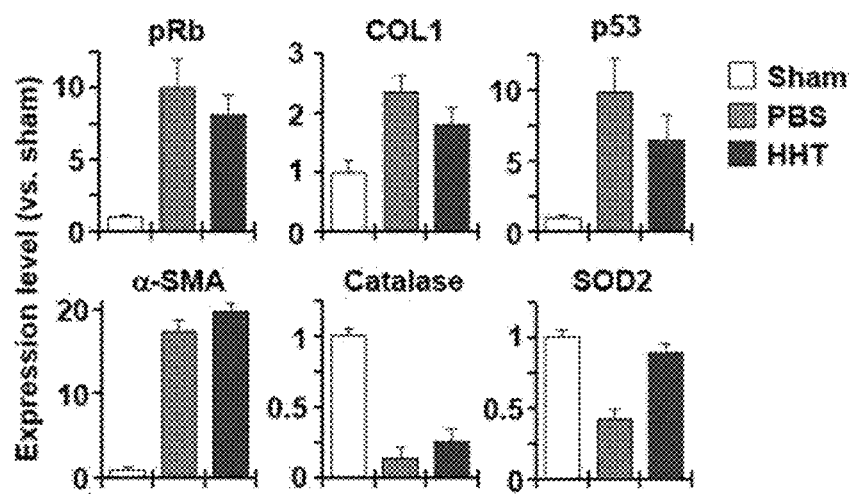

On the other hand, protein was separated from the tissue, and as a result of Western blot analysis of p16 as a cellular aging marker and 4-HNE as an oxidative stress marker, it was significantly reduced in the HHT group compared to that in the PBS group as shown in FIG. 8K, and It was confirmed that the expressions of pRb as a cell proliferation marker, type 1 collagen (COL1) as a fibrosis marker, and p53 as a cellular aging marker were decreased in the HHT group compared to those in the PBS group as shown in FIG. 8K, and the expression of the antioxidant enzymes catalase and SOD2 was found to be increased in the HHT group compared to that in the PBS group as shown in FIG. 8M.

From the above results, it was confirmed that homoharringtonine has an effect of inhibiting renal fibrosis induced by ischemia-reperfusion injury of the kidney.

<EXAMPLE 4> CONFIRMATION OF EFFICACY OF HOMOHARRINGTONINE ON PERITONEAL FIBROSIS INDUCED BY CHLORHEXIDINE GLUCONATE (CHG)

Peritoneal fibrosis is a side effect that occurs frequently in patients who have undergone peritoneal dialysis, and may cause a problem of reducing peritoneal dialysis efficiency.

Long-term peritoneal dialysis increases reactive oxygen species by components of peritoneal dialysis fluid, and induces peritoneal fibrosis due to chronic inflammation. In this process, epithelial to mesenchymal transition of peritoneal mesenchymal cells by TGF-β1 is known to play an important role, and TGF-β1 is well known to induce cellular aging.

In order to confirm the effect of homoharringtonine on the peritoneal fibrosis, a 0.1% CHG solution was injected intraperitoneally for 20 days at intervals of 2 days, and homoharringtonine or DMSO-phosphate buffer solution was injected intraperitoneally from the 9th day.

Abdominal wall tissue specimens were prepared, and hematoxylin-eosin staining and trichrome staining were performed, and then the thickness of the peritoneal mesothelial cell layer and the degree of peritoneal fibrosis were analyzed.

Figure 9C:
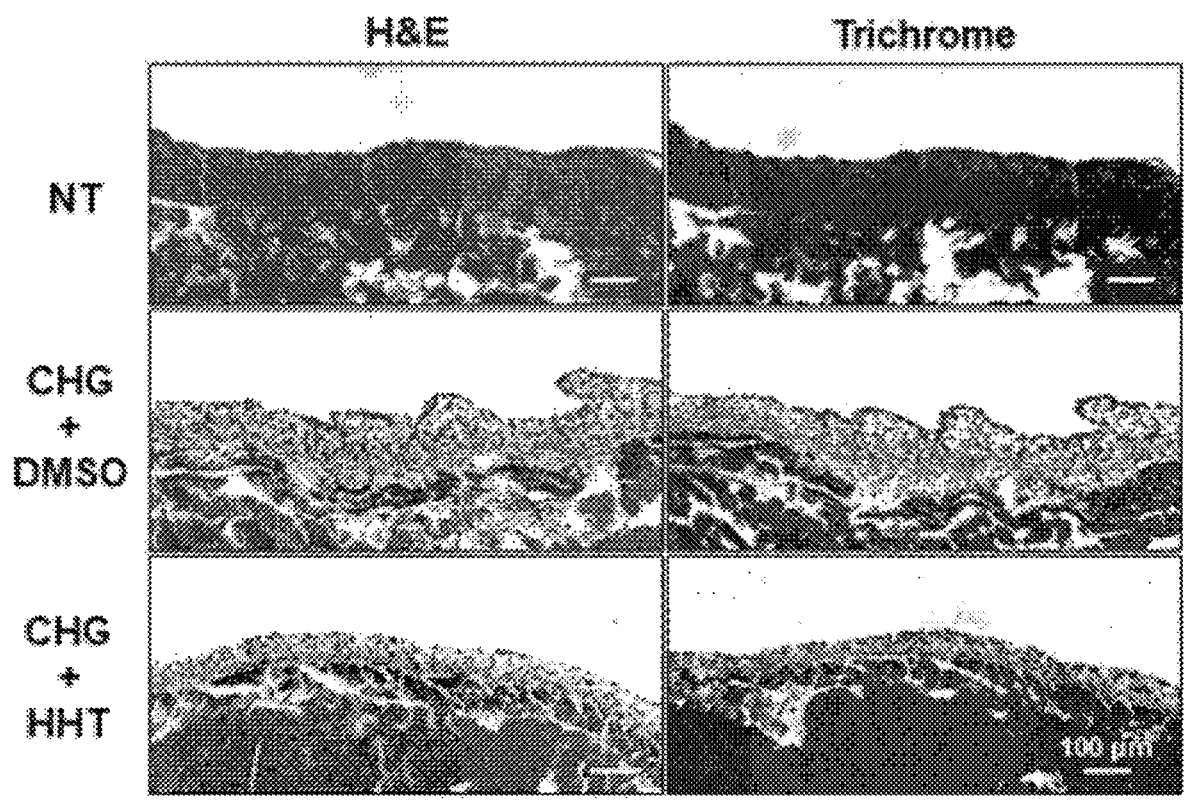
Figure 9D:
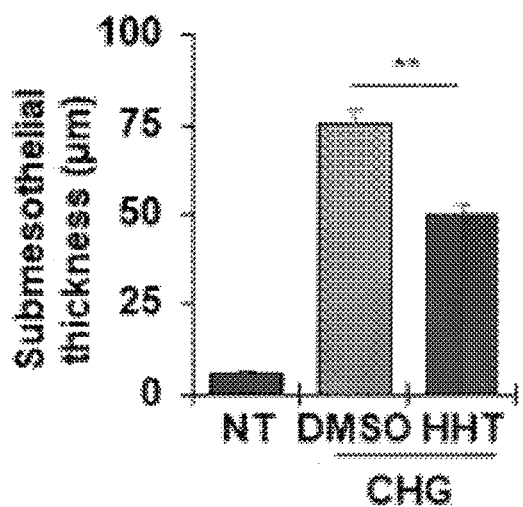

As a result, it was confirmed that the thickness of the peritoneal mesothelial cell layer in the homoharringtonine-treated group (HHT group) was significantly reduced compared to that in the DMSO-phosphate buffer solution (DMSO group) as shown in FIG. 9C and FIG. 9D, and the degree of fibrosis was also decreased.

From the above results, it was confirmed that homoharringtonine inhibits peritoneal fibrosis induced by CHG.

While the present invention has been particularly described with reference to specific examples thereof, it is apparent that this specific description is only a preferred example and that the scope of the present invention is not limited thereby to those skilled in the art. That is, the practical scope of the present invention is defined by the appended claims and their equivalents.

The invention claimed is:

1. A method of treating a renal cell cancer and a renal fibrosis comprising administering a pharmaceutical composition comprising homoharringtonine as an active ingredient to a subject in need of the treating the renal cell cancer and the renal fibrosis,
wherein the renal cell cancer and the renal fibrosis are induced by a renal ischemia-reperfusion injury.

2. The method of claim 1, wherein the homoharringtonine selectively kills a senescent cell or restores function or morphology of the senescent cell to a normal cell to treat the renal cell cancer and the renal fibrosis.

3. A method of treating peritoneal fibrosis comprising administering a pharmaceutical composition comprising homoharringtonine as an active ingredient to a subject in need of the treating the peritoneal fibrosis,
wherein the peritoneal fibrosis is induced by chlorhexidine gluconate.

4. The method of claim 3, wherein the homoharringtonine selectively kills a senescent cell or restores function or morphology of the senescent cell to a normal cell to treat the peritoneal fibrosis.

* * * * *